United States Patent
Ram

(10) Patent No.: US 10,523,181 B2
(45) Date of Patent: Dec. 31, 2019

(54) SURFACE ACOUSTIC WAVE RFID SENSOR FOR MATERIAL AND STRUCTURE SENSING

(71) Applicant: EPITRONIC HOLDINGS PTE. LTD., Singapore (SG)

(72) Inventor: Ayal Ram, Singapore (SG)

(73) Assignee: EPITRONIC HOLDINGS PTE. LTD., Singapore (SG)

( * ) Notice: Subject to any disclaimer, the term of this patent is extended or adjusted under 35 U.S.C. 154(b) by 0 days.

(21) Appl. No.: 16/326,163

(22) PCT Filed: Jul. 10, 2017

(86) PCT No.: PCT/IB2017/054140
§ 371 (c)(1),
(2) Date: Feb. 15, 2019

(87) PCT Pub. No.: WO2018/037296
PCT Pub. Date: Mar. 1, 2018

(65) Prior Publication Data
US 2019/0190492 A1    Jun. 20, 2019

Related U.S. Application Data

(60) Provisional application No. 62/377,774, filed on Aug. 22, 2016.

(51) Int. Cl.
*H03H 9/64* (2006.01)
*H03H 9/02* (2006.01)
(Continued)

(52) U.S. Cl.
CPC ............. *H03H 9/642* (2013.01); *G01N 29/00* (2013.01); *G01N 29/2462* (2013.01);
(Continued)

(58) Field of Classification Search
CPC .... H03H 9/642; H03H 9/02535; G01N 29/00; G01N 29/2462; G01N 29/2481
(Continued)

(56) References Cited

U.S. PATENT DOCUMENTS

| 2004/0173816 A1* | 9/2004 | Saxler ................... H01L 27/20 257/195 |
| 2007/0139165 A1 | 6/2007 | Liu |
| 2014/0008658 A1 | 1/2014 | Siemieniec et al. |

FOREIGN PATENT DOCUMENTS

CN      105424780      3/2016

OTHER PUBLICATIONS

International Search Report PCT/IB2017/054140 completed Oct. 17, 2017; dated Oct. 30, 2017 5 pages.
(Continued)

*Primary Examiner* — Derek J Rosenau
(74) *Attorney, Agent, or Firm* — The Roy Gross Law Firm, LLC; Roy Gross

(57) ABSTRACT

The present application describes embodiments of a zero-power radio-frequency identification (RFID) sensor chip based on a combination of a surface acoustic wave (SAW) transducer and two-dimensional electron gas (2DEG) or two-dimensional holegas (2DHG) conducting structure, and its use as an ultrasensitive microphone for material and structure sensing. The SAW RFID sensor contains a piezoelectric substrate, on which a multilayer heterojunction structure is deposited. The heterojunction structure comprises at least two layers, a buffer layer and a barrier layer, wherein both layers are grown from III-V single-crystalline or polycrystalline semiconductor materials, such as Ga N/Al Ga N. Interdigitated transducers (IDTs) transducing SAWs are installed on top of the barrier layer. A conducting channel comprising a two-dimensional electron gas (2DEG), in case of two-layers configuration, or a two-dimensional hole gas (2DHG), in case of three-layers configuration, is formed at the interface between the buffer and barrier layers and provides electron or hole current in the system between the
(Continued)

non-ohmic (capacitively-coupled) source and drain contacts connected to the formed channel.

**20 Claims, 18 Drawing Sheets
(15 of 18 Drawing Sheet(s) Filed in Color)**

(51) Int. Cl.
    *G01N 29/00*     (2006.01)
    *G01N 29/24*     (2006.01)

(52) U.S. Cl.
    CPC ..... *G01N 29/2481* (2013.01); *H03H 9/02535* (2013.01); *G01N 2291/0423* (2013.01)

(58) Field of Classification Search
    USPC ...... 310/313 R, 313 A, 313 B, 313 C, 313 D
    See application file for complete search history.

(56) References Cited

OTHER PUBLICATIONS

Written Opinion of the International Searching Authority PCT/IB2017/054140 dated Oct. 30, 2017 8 pages.

International Preliminary Report on Patentability PCT/IB2017/054140 completed Nov. 19, 2018 44 pages.

Shigekawa et al, "Surface Acoustic Waves in Reverse-Biased AlGaN/GaN Heterostructures", IEEE Transactions on Electron Devices, IEEE Service Center, Piscataway, NJ, US, vol. 55, No. 7, Jul. 1, 2008, pp. 1585-159.

Pearton S J et al: "Topical REview: GaN-based diodes and transitors for chemical, gas, biologica and pressure sensing; Topical REview" Journal of Physics: Condensed Matter, Institute of Physics Publishing, Bristol, GB, vol. 16, No. 29, Jul. 28, 2004 (Jul. 28, 2004), pp. R961-R994.

Lalinskty et al., "AlGaN/GaN based SAW-HEMT structures for chemical gas sensors", Procedia Engineering, Elsevier, Amsterdam, NL, vol. 5, Jan. 1, 2010, pp. 152-155.

Kreft et al., "Surface Acoustic Waves and Nano-Electromechanical Systems", Acoustic Waves—From Microdevices to Helioseismology, Nov. 14, 2011, InTech, pp. 637-652.

Lalinskty et al., "AlGaN/GaN hetrostructure-based surface acoustic wave-structure for chemical sensors", Applied Surface Science, Elsevier, Amsterdam, NL, vol. 255. No. 3, Nov. 30, 2008.

Chuan-Yu Zhang et al: "Propogation characteristics of surface acoustic waves in single-electron transport devices and the electrical measurement" IEEE Transactions on Ultrasonics, Ferroelectrics and Frequency Control, IEEE, US vol. 58, No. 7, Jul. 1, 2011.

\* cited by examiner

Fig. 4  Ga-Face Polarity
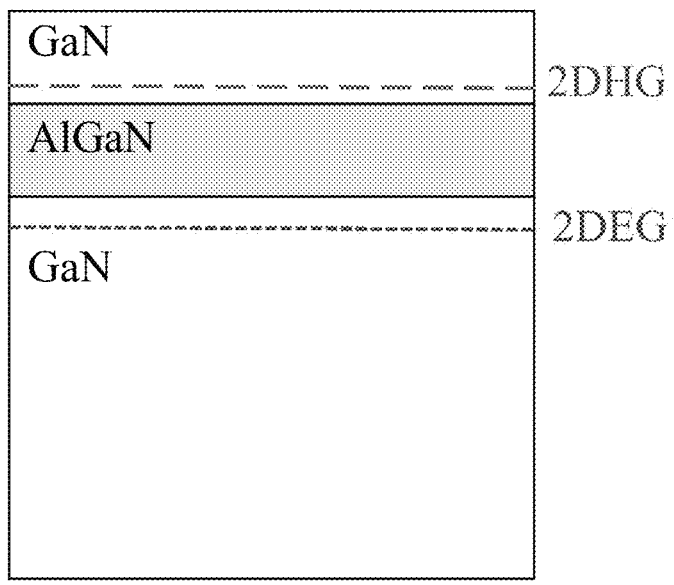
Fig. 5  N-Face Polarity
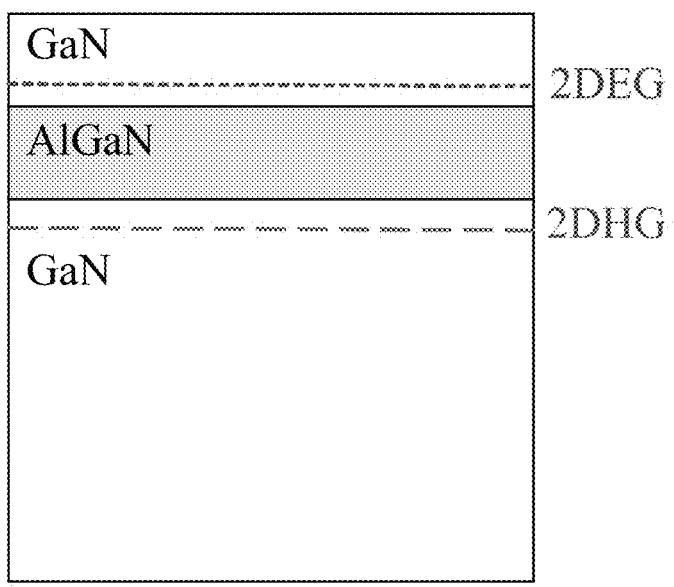

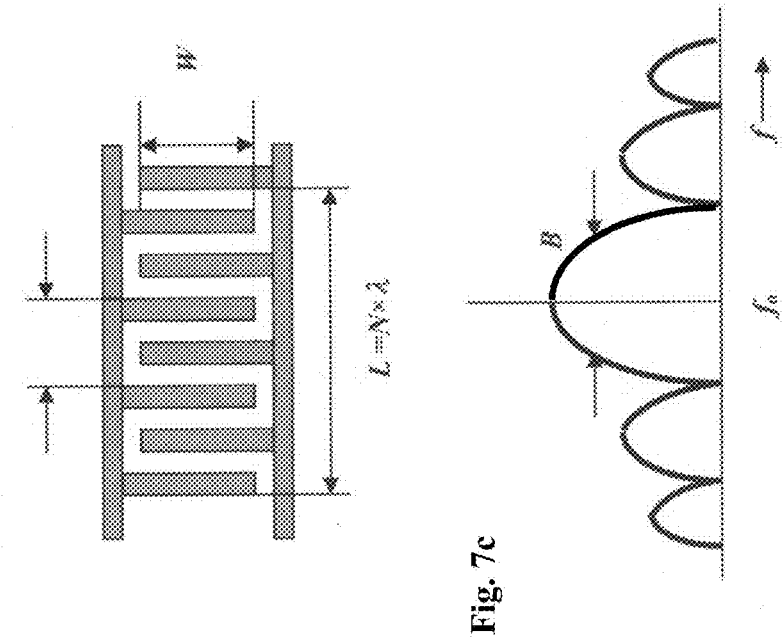
Fig. 7b
Fig. 7c
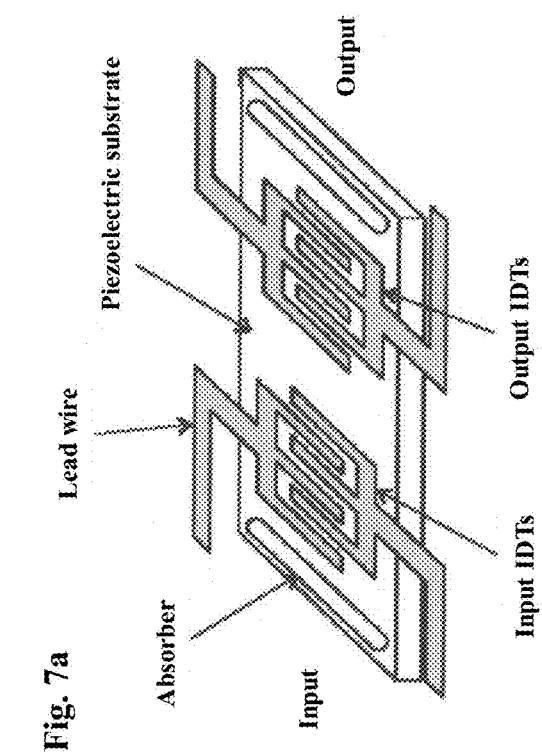
Fig. 7a

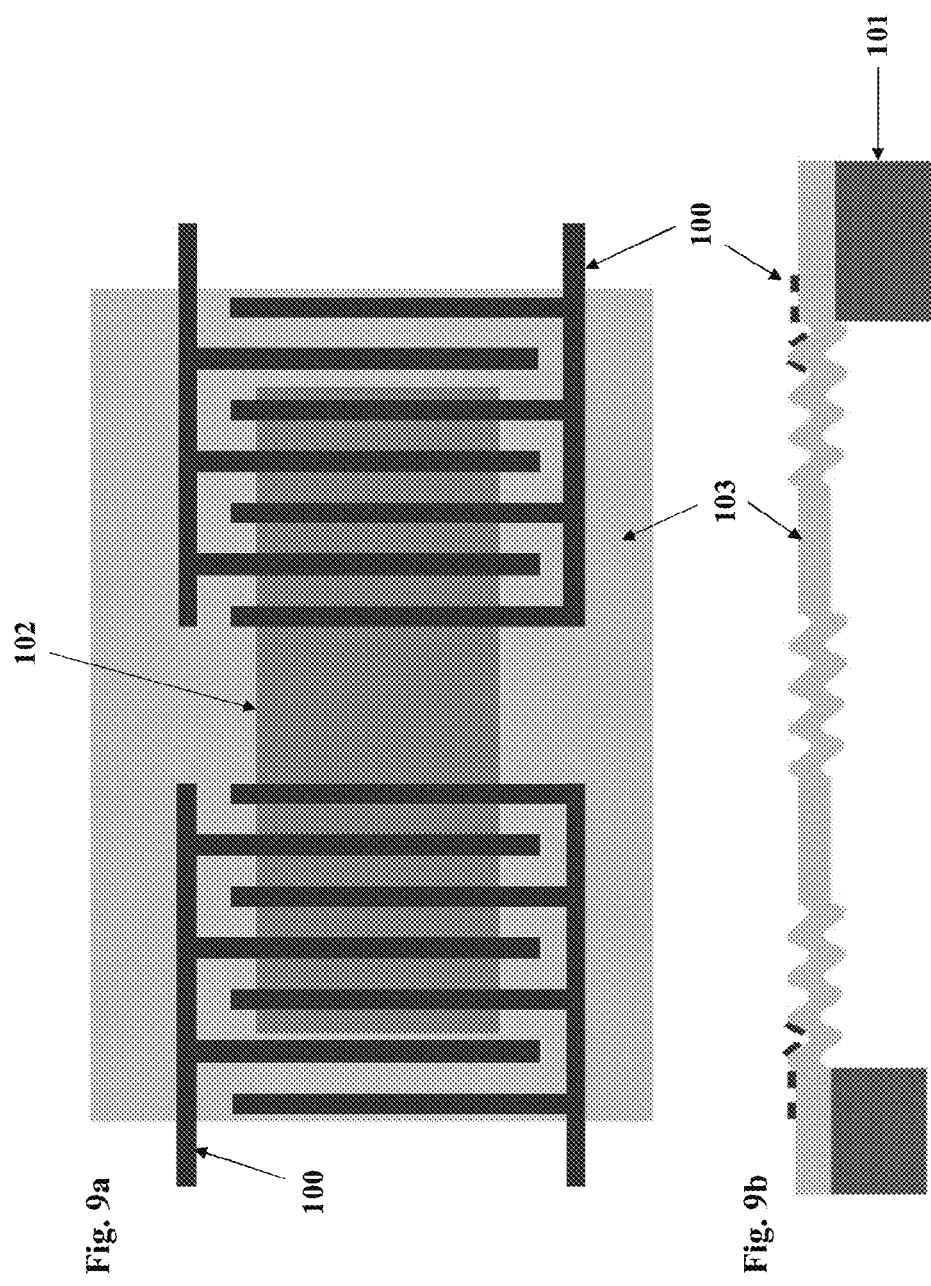

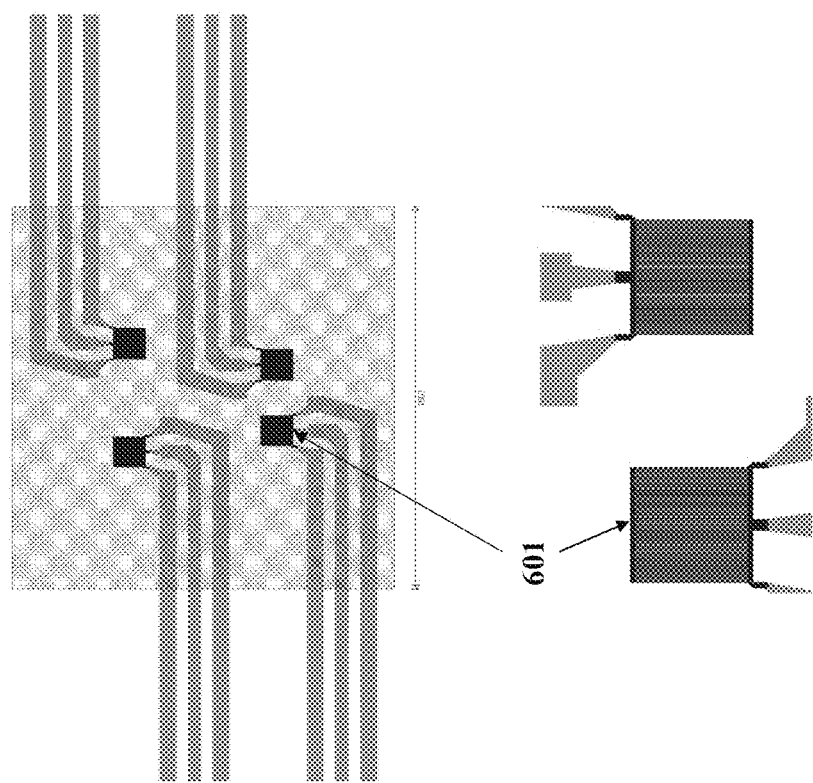
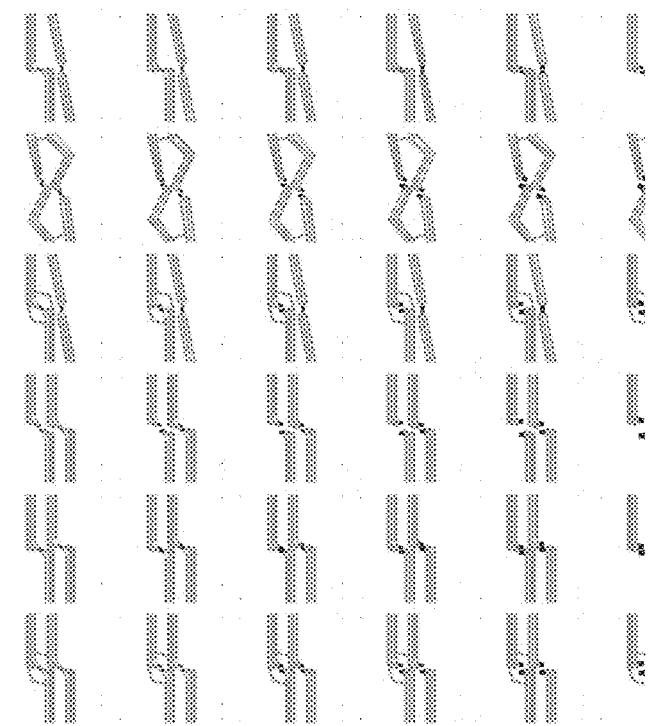
Fig. 11

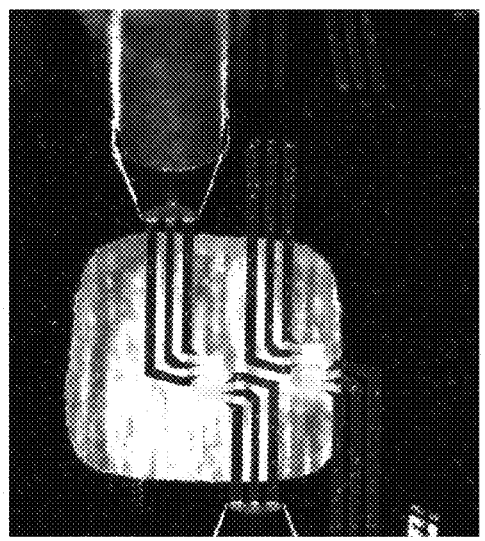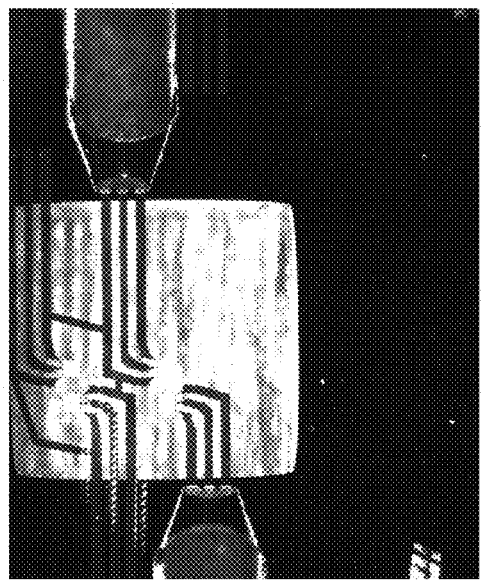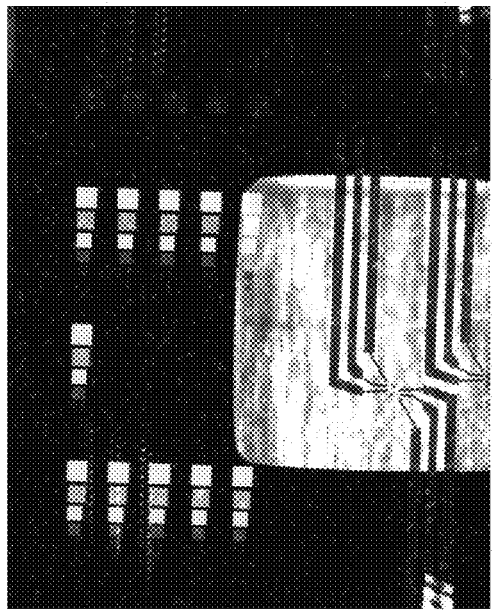
Fig. 13

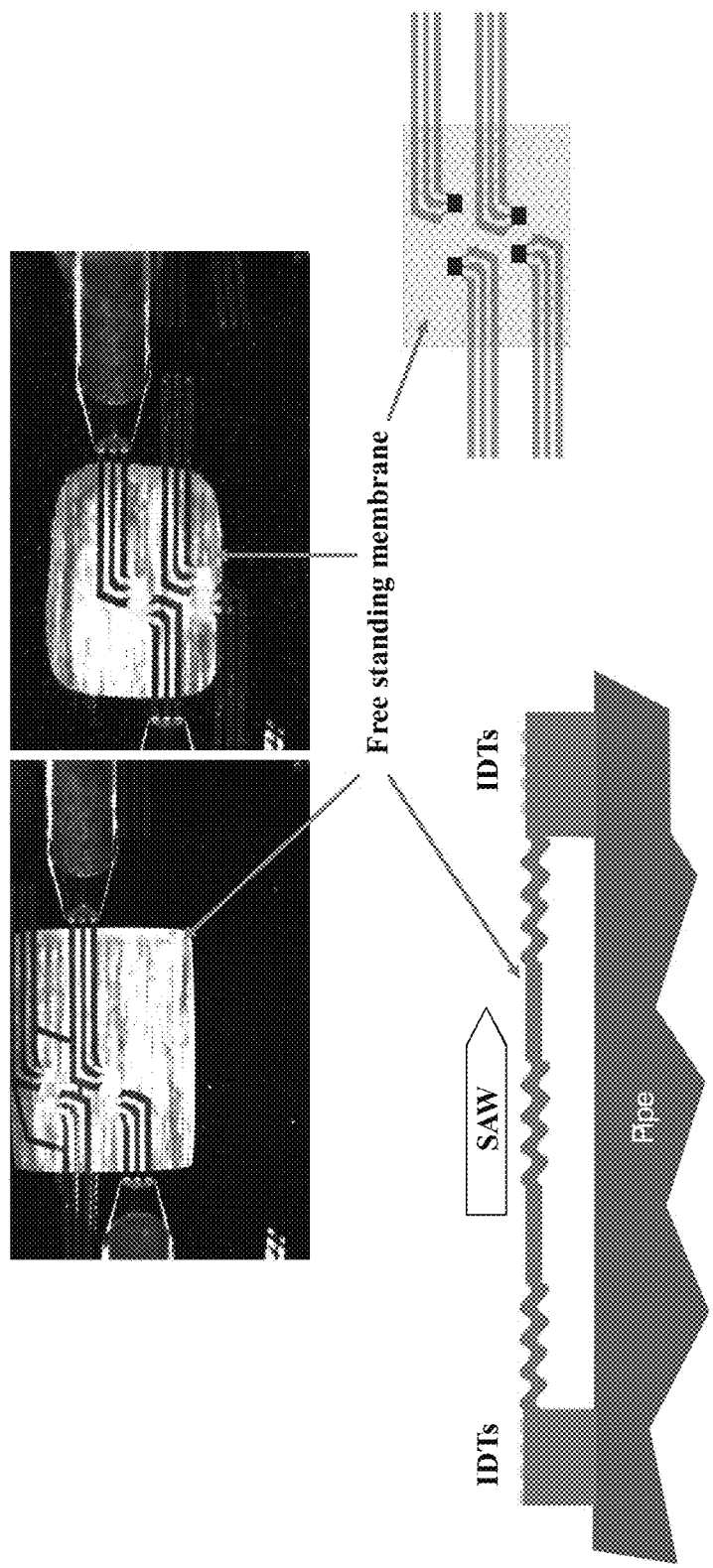

SURFACE ACOUSTIC WAVE RFID SENSOR FOR MATERIAL AND STRUCTURE SENSING

RELATED APPLICATIONS

This application is a National Phase of PCT Patent Application No. PCT/IB2017/054140 having International filing date of Jul. 10, 2017, which claims the benefit of priority of U.S. Provisional Application No. 62/377,774, filed on Aug. 22, 2016. The contents of the above applications are all incorporated by reference as if fully set forth herein in their entirety.

TECHNICAL FIELD

In general, the present application relates to the field of electronic sensors based on surface acoustic wave (SAW) transducers. In particular, the present application relates to the GaN/AlGaN SAW RFID sensor and its use in material and structure sensing.

BACKGROUND

Surface acoustic-wave (SAW) sensors play an important role in many fields of material sensing and industrial applications. In general, a surface acoustic wave is an acoustic wave that propagates along the surface of a certain (piezoelectric) material. It is generated by interdigitated transducer (IDT) electrodes (or "fingers"), which are special periodic metallic bars deposited on a piezoelectric material. When any sinusoidal wave having a period equal to the period of the IDT electrodes is applied, mechanical vibration occurs beneath the IDT electrodes, thereby generating an acoustic wave, which is perpendicular to the geometry of the IDT bars. This acoustic wave propagates on the surface of the piezoelectric material away from the IDT electrodes in both directions.

The acoustic wave generated by the IDTs is localised in the surface region and penetrates the bulk piezoelectric material only to a wavelength deep region. That is why the SAW has a very high energy density at the surface, which gives the name "surface acoustic wave". The SAW propagates in a piezoelectric material approximately $10^5$ times slower than a regular electromagnetic wave. Consequently, the SAW wavelength in the piezoelectric material is $10^5$ times smaller than the wavelength of an electromagnetic wave, making the SAW-based sensor a very compact device.

Fabrication of the SAW sensors requires either deposition or etching of the metallic IDTs on a piezoelectric material, and it uses the CMOS process technology, which allows a large scale manufacture. The factors that can affect the piezoelectric material surface condition include pressure, temperature, humidity and mass loading. Accordingly, SAW sensors can be used as pressure, temperature, humidity sensors, and as sensors capable of detecting mass changes or electric field alterations at the surface. A MEMS-CMOS technology facilitates the integration of the SAW sensors and their data processing circuits. Specially designed SAW sensors can also be used in a passive mode without need for batteries. An RFID antenna can be added to the input IDT electrode and the signal received by the antenna can then stimulate the SAW used for sensing as mentioned before. These are actually the SAW sensors using RFID tags. The ultrahigh sensitivity, compact nature, ease of fabrication and wireless operation make these sensors very attractive for material sensing.

SUMMARY

The present application describes embodiments of a microelectronic sensor based on a combination of a two-dimensional electron gas (2DEG) or two-dimensional hole gas (2DHG) conducting structure and surface acoustic wave (SAW) transducer. In some embodiments, the sensor may contain a piezoelectric substrate, on which a multilayer heterojunction structure may be deposited. This heterojunction structure may comprise at least two layers, a buffer layer and a barrier layer, wherein both layers are grown from III-V single-crystalline or polycrystalline semiconductor materials. Interdigitated transducers (IDTs) transducing surface acoustic waves may be installed on top of the barrier layer.

A conducting channel comprising a two-dimensional electron gas (2DEG) or a two-dimensional hole gas (2DHG) is formed at the interface between the buffer and barrier layers and may provide electron or hole current in the system between source and drain electrodes. In a particular embodiment, the heterojunction structure may be a three-layer structure consisting of two buffer layers and one barrier layer squeezed between said buffer layers like in a sandwich. This may lead to formation of the two-dimensional hole gas (2DHG) in the top buffer layer above the barrier layer which results in reversing polarity of the structure. An optional dielectric layer may be deposited on top of the heterojunction structure. The open gate area of the 2DEG/2DHG is formed between the source and drain areas as a result of recessing or growing of the top layer to a specific thickness.

The IDTs may be made from GaN/AlGaN semiconductor materials and from metal turning the IDTs into the 2DEG/2DHG conducting structures. In a particular embodiment, the piezoelectric substrate may be optionally placed on a GaN/AlGaN free-standing membrane resulting in a SAW-FBAR (Film Bulk Acoustic Resonators) configuration, for achieving ultra-sensitivity. In another embodiment, the sensor may be based on a regular silicon piezoelectric substrate firmly connected to a structural material being tested. In case of any stress or mechanical deformation of this structural material, the piezoelectric GaN/AlGaN stack will also be stressed or deformed, thereby changing the SAW propagation parameters. This is because of the piezoelectric polarization effect within the SAW structures resulting in change of the S21 transfer parameter on the IDT receiver.

The source and drain non-ohmic (i.e. capacitively-coupled) contacts are connected to the 2DEG/2DHG channel and to electrical metallizations, the latter are placed on top of the sensor and connect it to an electric circuit of the sensor. Since the source and drain contacts are non-ohmic, the DC readout cannot be carried out. In order to electrically contact the 2DEG/2DHG channel underneath, about 5-20 nm bellow the metallizations, the AC-frequency regime must be used. In other words, the AC readout or impedance measurements of the electric current flowing through the 2DEG/2DHG-channel should be performed in this particular case. The capacitive coupling of the non-ohmic metal contacts with the 2DEG/2DHG channel is normally induced at the frequency higher than 30 kHz.

In some embodiments, the multilayer heterojunction substrate of the present application may be grown from any available III-V single-crystalline or polycrystalline semiconductor materials, for example, GaN/AlGaN, GaN/AlN, GaN/InN, GaN/InAlN, InN/InAlN, GaN/InAlGaN, GaAs/AlGaAs and $LaAlO_3/SrTiO_3$. In a specific case of the substrate grown from GaN/AlGaN, it has been experimentally and surprisingly found that the highest sensitivity of the sensor is achieved when thickness of the top recessed layer (GaN buffer layer or AlGaN barrier layer) in the open gate area between the source and drain contacts is 5-9 nm, preferably 6-7 nm, more preferably 6.2-6.4 nm. This recessed layer thickness corresponds to the pseudo-conducting current range between normally-on and normally-off operation mode of the 2DEG/2DHG conducting channel. In addition, surface roughness of the top recessed layer within the open gate area between the source and drain contacts has a roughness of about 0.2 nm or less, preferably 0.1 nm or less, more preferably 0.05 nm.

Further, in some embodiments, the present application provides the zero-power SAW RFID sensor, which is based on the GaN/AlGaN heterostructure, and its use in material and structure sensing. In another embodiment, the sensor is a zero-power sensor remotely powered with the RF-energy and RFID-coded via the orthogonal frequency coding (OFC) method.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Disclosed embodiments will be understood and appreciated more fully from the following detailed description taken in conjunction with the appended figures. The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

FIG. 1a: positive gate potential ($+V_G$) is much higher than threshold voltage ($V_T$), FIG. 1b: 0V gate potential, and FIG. 1c: negative gate potential ($-V_G$) is below threshold voltage ($V_T$).

FIG. 4 schematically shows the formation of the 2DEG and 2DHG conducting channels in the Ga-face three-layer AlGaN/GaN PC-HEMT structure.

FIG. 5 schematically shows the formation of the 2DEG and 2DHG conducting channels in the N-face three-layer AlGaN/GaN PC-HEMT structure.

FIG. 7a schematically shows the input interdigitated transducer (IDT)-based SAW device.

FIG. 7b schematically shows the IDT and its characteristic parameters: length (L), width (W) and acoustic wavelength ($\lambda$).

FIG. 7c shows the bandwidth (B) of the SAW as a function of the number of the IDTs and the frequency (f), where $f_0$ is the centre frequency.

FIGS. 9a-9c schematically show a basic topology of the sensor of an embodiment with free standing membranes, wherein lines (100) show the metal IDT structures, area (102) shows the PC-HEMT-like structure and area (103) shows the GaN/AlGaN-layered substrate.

FIG. 11 shows the photolithographic layout masks of the 2DEG-based SAW resonator using the standard configuration with two symmetrical IDT structures (fingers).

FIG. 13 shows the microscope images of the fabricated SAW resonators of FIGS. 11-12 on the free-standing GaN/AlGaN membranes having the unstructured 2DEG with the DRIE-removed Si substrate.

FIG. 16 shows the microscope images of the SAW resonators as in FIG. 11, and further highlights the free-standing FBAR membrane in the FBAR-SAW configuration of the sensor.

DETAILED DESCRIPTION

Figure 1:
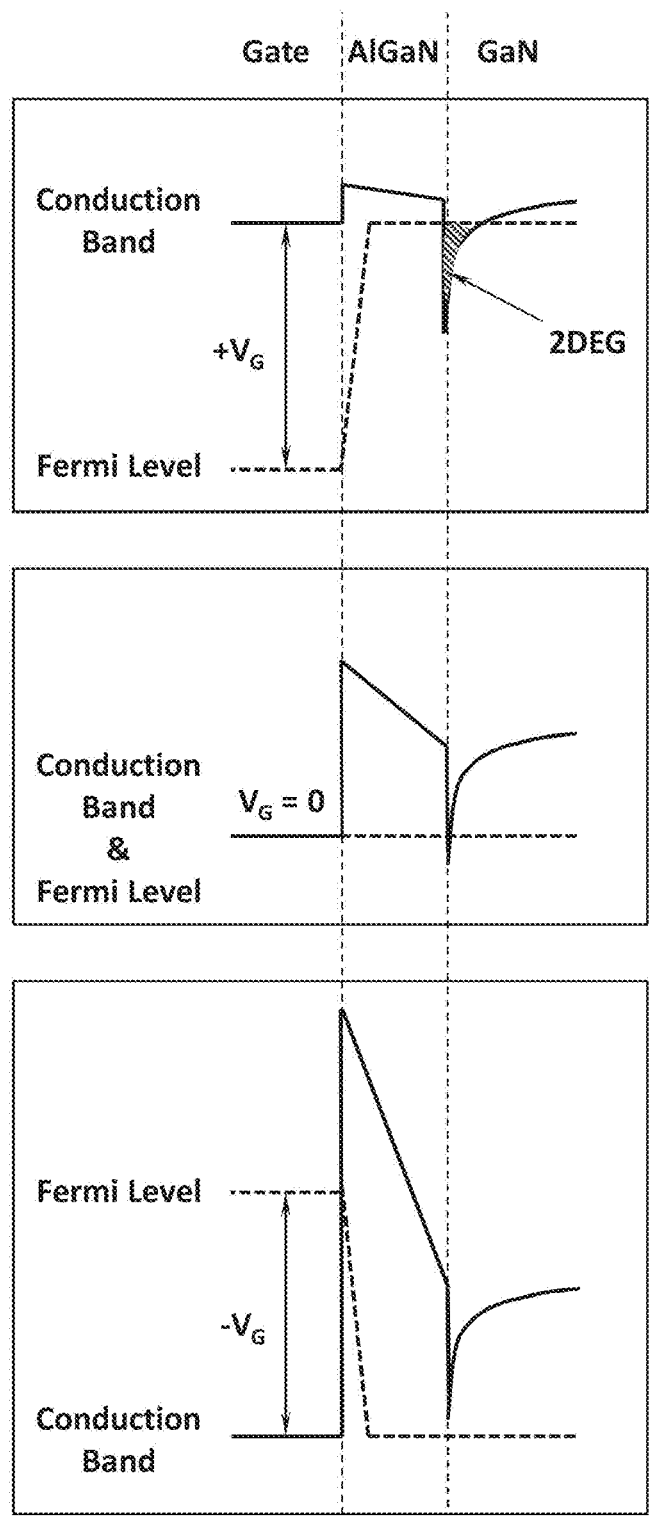
FIG. 1 schematically shows the quantum well at three different biasing conditions.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, is "open ended" and means the elements recited, or their equivalent in structure or function, plus any other element or elements which are not recited. It should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. Also, the scope of the expression "a method comprising the steps x and z" should not be limited to methods consisting only of these steps.

Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The polarization doped high-electron-mobility transistor (HEMT) is a field effect transistor (FET) in which two layers of different bandgap and polarisation field are grown upon each other forming the heterojunction structure. In one aspect, the sensor of the present application contains a piezoelectric substrate comprising the HEMT-like multi-layer heterojunction structure. This structure is essentially based on at least two layers of III-V semiconductor materials, such as gallium nitride (GaN) and aluminium gallium nitride (AlGaN). As a consequence of the discontinuity in the polarisation field, surface charges are created at the interface between the layers of the heterojunction structure. If the induced surface charge is positive, electrons will tend to compensate the induced charge resulting in the formation of the channel. Since the channel electrons are confined in a quantum well in an infinitely narrow spatial region at the interface between the layers, these electrons are referred to as a two-dimensional electron gas (2DEG). This special confinement of the channel electrons in the quantum well actually grants them two-dimensional features, which strongly enhance their mobility surpassing the bulk mobility of the material in which the electrons are flowing.

FIGS. 1a-1c schematically shows the quantum well at three different biasing conditions starting from the positive gate potential ($V_G$), much higher than the threshold voltage ($V_T$), and going down to the 0V gate potential and further to the negative values below the threshold voltage. The $V_T$ is defined as a voltage, which is required to populate electrons at the interface between the GaN layer and the AlGaN layers, thereby creating conductivity of the 2DEG channel. Since the 2DEG channel electrons occupy energy levels below the Fermi level, the Fermi level in a quantum well is located above several energy levels when $V_G \gg V_T$ (FIG. 1a). This enables high population of channel electrons and consequently, high conductivity. The 2DEG channel is turned on in this case. However, when $V_G$ decreases to 0V (FIG. 1b), the Fermi level also drops with respect to the quantum well. As a result, much fewer electron energy levels are populated and the amount of the 2DEG channel electrons significantly decreases. When $V_G$ much less than $V_T$ (FIG. 1c), all electron energy levels are above the Fermi level, and there is no the 2DEG electrons below the gate. This situation is called "channel depletion", and the channel is turned off.

Many commercially available HEMTs based on the layers of III-V semi-conductor materials have a negative value of $V_T$, resulting in a "normally-on" operation mode at 0V gate potential. They are called "depletion-mode" semiconductor transistors and used in various power switching applications when the negative voltage must be applied on the gate in order to block the current. However, for safe operation at high voltage or high power density, in order to reduce the circuit complexity and eliminate standby power consumption, the transistors with "normally-off" characteristics are preferred. The high voltages and high switching speeds allow smaller, more efficient devices, such as home appliances, communications and automobiles to be manufactured. To control the density of electrons in the 2DEG channel and to switch the HEMT on and off, the voltage at the gate of the transistor is normally regulated.

Several techniques to manufacture the normally-off semiconductor structures have been reported. Burnham et al (2010) proposed normally-off structures of the recessed gate type. In this structure, the AlGaN barrier layer is etched and the gate is brought closer to the interface between the AlGaN barrier layer and the GaN buffer layer. As the gate approaches the interface between the layers, the $V_T$ increases. Thus, the normally-off operation of the 2DEG conducting channel is achieved once the depletion region reaches the interface and depletes the 2DEG channel at zero gate voltage. The major advantages of these structures are relatively lower power consumption, lower noise and simpler drive circuits. They are currently used, for example, in microwave and millimetre wave communications, imaging and radars.

Chang et al (2009) proposed instead of etching the relatively thick barrier layer to approach the AlGaN/GaN interface, to use a very thin AlGaN barrier. This structure also achieves the normally-off operation of the 2DEG channel by approaching the gate towards the AlGaN/GaN interface. Chen et al (2010) proposed to use the fluorine-based plasma treatment method. Although many publications have adopted various methods to achieve normally-off devices with minimum impact on the drain current, they unfortunately sacrificed device turn-on performance.

Figure 2:
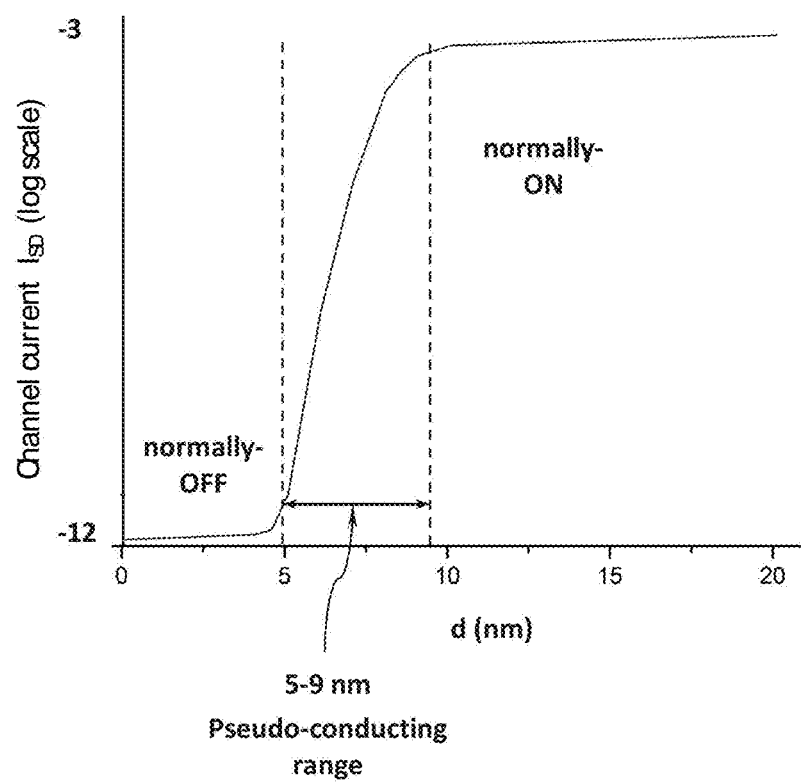
FIG. 2 schematically shows the dependence of the source-drain current (a charge carrier density) induced inside the 2DEG channel of a GaN/AlGaN HEMT on the thickness of the AlGaN barrier layer recessed in the open gate area.

FIG. 2 shows the dependence of the source-drain current (a charge carrier density) on the recessed barrier layer thickness. As seen from the plot, structures that have a thickness of the barrier layer larger than 9 nm form normally-on 2DEG channels. In such structures, due to the inherent polarisation effects present in the III-V materials, a thin sheet of charges is induced at the top and bottom of the interfaces of the barrier layer. As a result, a high electric field is induced in the barrier layer, and surface donor states at the top interface start donating electrons to form the 2DEG channel at the proximity of the hetero-junction interface without the application of a gate bias. These structures therefore constitute normally-on devices. On the other hand, the structures that have a thickness of the barrier layer lower than about 5 nm constitute normally-off devices.

The present application describes embodiments of a microelectronic sensor or sensor chip based on a combination of a two-dimensional electron gas (2DEG) or two-dimensional hole gas (2DHG) structure and surface acoustic wave (SAW) transducer. In some embodiments, the sensor may contain a piezoelectric substrate, on which the multilayer heterojunction structure may be deposited. This heterojunction structure may comprise at least two layers, a buffer layer and a barrier layer, wherein both layers are grown from the aforementioned III-V single-crystalline or polycrystalline semiconductor materials. Interdigitated transducers (IDTs) transducing surface acoustic waves may be installed on top of the barrier layer. In some embodiments, the multilayer heterojunction structure of the present application may be grown from any available III-V single-crystalline or polycrystalline semiconductor materials, such as GaN/AlGaN, GaN/AlN, GaN/InN, GaN/InAlN, InN/InAlN, GaN/InAlGaN, GaAs/AlGaAs and LaAlO$_3$/SrTiO$_3$. In a specific case of the substrate grown from GaN/AlGaN, it has been experimentally found that the highest sensitivity of the sensor is achieved when thickness of the top recessed layer (GaN buffer layer or AlGaN barrier layer) in the open gate area between the source and drain contacts is 5-9 nm, preferably 6-7 nm, more preferably 6.2-6.4 nm. In addition, it was also found that the sensor exhibits its highest sensitivity when surface roughness of the top recessed layer is about 0.2 nm or less, preferably 0.1 nm or less, more preferably 0.05 nm.

Thus, the top layer recessed or grown in the open gate area to 5-9 nm must be optimised for significantly enhancing sensitivity of the sensor. This specific thickness of the barrier layer was surprisingly found to correspond to the "pseudo-conducting" current range between normally-on and normally-off operation modes of the 2DEG channel and requires further explanation.

"Pseudo-contacting" (to distinguish from normally-conducting) current range of the 2DEG channel is defined as an operation range of the channel between its normally-on and normally-off operation modes. "Trap states" are states in the band-gap of a semiconductor which trap a carrier until it recombines. "Surface states" are states caused by surface reconstruction of the local crystal due to surface tension caused by some crystal defects, dislocations, or the presence of impurities. Such surface reconstruction often creates "surface trap states" corresponding to a surface recombination velocity. Classification of the surface trap states depends on the relative position of their energy level inside the band gap. The surface trap states with energy above the Fermi level are acceptor-like, attaining negative charge when occupied. However, the surface trap states with energy below the Fermi level are donor-like, positively charged when empty and neutral when occupied. These donor-like surface trap states are considered to be the source of electrons in the formation of the 2DEG channel. They may possess a wide distribution of ionization energies within the band gap and are caused by redox reactions, dangling bonds and vacancies in the surface layer. A balance always exists between the 2DEG channel density and the number of ionised surface donors which is governed by charge neutrality and continuity of the electric field at the interfaces.

Thus, the donor-like surface traps at the surface of the barrier layer are one of the most important sources of the 2DEG in the channel. However, this only applies for a specific barrier layer thickness. In a relatively thin barrier layer, the surface trap state is below the Fermi level. However, as the barrier layer thickness increases, the energy of the surface trap state approaches the Fermi energy until it coincides with it. The thickness of the barrier layer corresponding to such situation is defined as "critical". At this point, electrons filling the surface trap state are pulled to the channel by the strong polarisation-induced electric field found in the barrier to form the 2DEG instantly.

If the surface trap states are completely depleted, further increase in the barrier layer thickness will not increase the 2DEG density. Actually, if the 2DEG channel layer fails to stretch the barrier layer, the later will simply relax. Upon relaxation of the barrier layer, many crystal defects are created at the interface between the buffer and barrier layers, and the piezoelectric polarisation instantly disappears causing deterioration in the 2DEG density.

Figure 3:
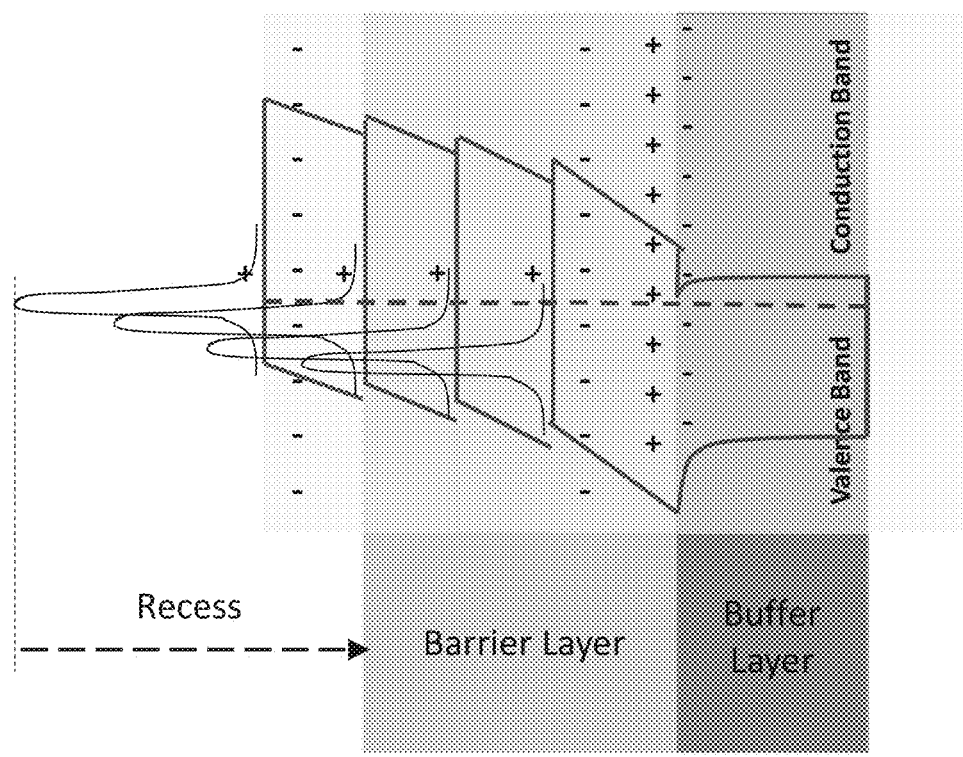
FIG. 3 illustrates a theory behind the 2DEG formation (charge neutrality combined with the lowest energy level) at the conduction band discontinuity.

In order to illustrate the above phenomenon of the pseudo-conducting current, reference is now made to FIGS. 2 and 3. As described above, FIG. 2 shows the dependence of the source-drain current (a charge carrier density) on the recessed AlGaN barrier layer thickness. Energy equilibrium between the donor surface trap states and AlGaN tunnel barrier leads to the 2DEG formation (charge neutrality combined with the lowest energy level) at the conduction band discontinuity. As explained above, decrease in the thickness of the barrier layer results in increase of the energy barrier. As a result, the ionisable donor-like surface trap states, which are responsible for electron tunneling from the surface to 2DEG, drift bellow the Fermi level, thereby minimizing the electron supply to the 2DEG channel. This theoretical situation is further illustrated in FIG. 3. Therefore, the recess of the AlGaN layer from 9 nm to 5 nm leads to huge drop in conductivity of the two-dimensional electron gas for six orders of magnitude.

Thus, the mechanism of the 2DEG depletion based on recessing the barrier layer is strongly dependent on the donor-like surface trap states (or total surface charge). As the thickness of the barrier layer decreases, less additional external charge is needed to apply to the barrier layer surface in order to deplete the 2DEG channel. There is a critical (smallest) barrier thickness, when the 2DEG channel is mostly depleted but still highly conductive due to a combination of the energy barrier and the donor surface trap states energy. At this critical thickness, even the smallest energy shift at the surface via any external influence, for example an acoustic wave propagating along the surface, leads immediately to the very strong 2DEG depletion. As a result, the surface of the barrier layer at this critical thickness is extremely sensitive to any smallest change in the electrical field of the surroundings.

Thus, recess of the barrier layer from 9 nm down to 5 nm significantly reduced the 2DEG density, brought the sensor to the "near threshold" operation and resulted in highly increased surface charge sensitivity. The specific 5-9 nm thickness of the barrier layer responsible for the pseudo-conducting behaviour of the 2DEG channel gives the sensor an incredible sensitivity.

In addition to the recessed or grown top barrier layer thickness, roughness of the barrier layer surface is another very important parameter that has not been previously disclosed. It has been surprisingly found that the roughness of the AlGaN barrier layer surface bellow 0.2 nm prevents scattering of the donor-like surface trap states.

Thus, combination of these two features: 5-9 nm thickness of the AlGaN barrier layer and strongly reduced roughness of its surface make the sensor incredibly sensitive.

In a further aspect, the hetero-junction structure may be a three-layer structure consisting of two buffer layers and one barrier layer squeezed between said buffer layers like in a sandwich, wherein the top layer is a buffer layer. This may lead to formation of the two-dimensional hole gas (2DHG) in the top buffer layer above the barrier layer which results in reversing polarity of the transistor compared to the two-layer structure discussed above.

In general, polarity of III-V nitride semiconductor materials strongly affects the performance of the transistors based on these semiconductors. The quality of the wurtzite GaN materials can be varied by their polarity, because both the incorporation of impurities and the formation of defects are related to the growth mechanism, which in turn depends on surface polarity. The occurrence of the 2DEG/2DHG and the optical properties of the hetero-junction structures of nitride-based materials are influenced by the internal field effects caused by spontaneous and piezo-electric polarizations. Devices in all of the III-V nitride materials are fabricated on polar {0001} surfaces. Consequently, their characteristics depend on whether the GaN layers exhibit Ga-face positive polarity or N-face negative polarity. In other words, as a result of the wurtzite GaN materials polarity, any GaN layer has two surfaces with different polarities, a Ga-polar surface and an N-polar surface. A Ga-polar surface is defined herein as a surface terminating on a layer of Ga atoms, each of which has one unoccupied bond normal to the surface. Each surface Ga atom is bonded to three N atoms in the direction away from the surface. In contrast, an N-polar surface is defined as a surface terminating on a layer of N atoms, each of which has one unoccupied bond normal to the surface. Each surface N atom is also bonded to three Ga atoms in the direction away from the surface. Thus, the N-face polarity structures have the reverse polarity to the Ga-face polarity structures.

As described above for the two-layer heterojunction structure, the barrier layer is always placed on top of the buffer layer. The layer which is therefore recessed is the barrier layer, specifically the AlGaN layer. As a result, since the 2DEG is used as the conducting channel and this conducting channel is located slightly below the barrier layer (in a thicker region of the GaN buffer layer), the hetero-junction structure is grown along the {0001}-direction or, in other words, with the Ga-face polarity. However, as explained above, the physical mechanism that leads to the formation of the 2DEG is a polarisation discontinuity at the AlGaN/GaN interface, reflected by the formation of the polarisation-induced fixed interface charges that attract free carriers to form a two-dimensional carrier gas. It is a positive polarisation charge at the AlGaN/GaN interface that attracts electrons to form 2DEG in the GaN layer slightly below this interface.

As noted above, polarity of the interface charges depends on the crystal lattice orientation of the hetero-junction structure, i.e. Ga-face versus N-face polarity, and the position of the respective AlGaN/GaN interface in the hetero-junction structure (above or below the interface). Therefore, different types of the accumulated carriers can be present in the hetero-junction structure of the embodiments.

In case of the three-layer hetero-junction structure, there are four possible configurations:

Ga-Face Polarity
1) The Ga-face polarity is characterised by the 2DEG formation in the GaN layer below the AlGaN barrier layer. This is actually the same two-layer configuration as described above, but with addition of the top GaN layer. In this configuration, the AlGaN barrier layer and two GaN buffer layers must be nominally undoped or n-type doped.
2) In another Ga-face configuration shown in FIG. 4, in order to form the conducting channel comprising a two-dimensional hole gas (2DHG) in the top GaN layer above the AlGaN barrier layer in the configuration, the AlGaN barrier layer should be p-type doped (for example, with Mg or Be as an acceptor) and the GaN buffer layer should be also p-type doped with Mg, Be or intrinsic.

N-Face Polarity
3) The N-face polarity is characterised by the 2DEG formation in the top GaN layer above the AlGaN barrier layer, as shown in FIG. 5. In this case, the AlGaN barrier layer and two GaN buffer layers must be nominally undoped or n-type doped.
4) The last configuration assumes that the 2DHG conducting channel is formed in the buffer GaN layer below the AlGaN barrier layer. The top GaN layer may be present (three-layer structure) or not (two-layer structure) in this case. The AlGaN barrier layer must be p-type doped (for example, with Mg or Be as an acceptor) and the bottom GaN layer should be also p-type doped with Mg, Be or intrinsic.

Thus, there are four hetero-junction three-layer structures implemented in the transistor of the embodiments, based on the above configurations:
A. Ga-Face GaN/AlGaN/GaN heterostructure with the 2DEG formed in the GaN buffer layer below the AlGaN barrier layer. In this case, the top GaN layer may be omitted to obtain the two-layer structure. For the three-layer structure, the top GaN layer must be recessed to 1-9 nm thickness in the open gate area or grown with this low thickness, with the roughness below 0.2 nm, and the thickness of the AlGaN barrier can be adjusted properly during growth B. Ga-Face GaN/AlGaN/GaN heterostructure with the 2DHG conducting channel formed in the top GaN layer above the AlGaN barrier layer. The top GaN layer must be recessed to 5-9 nm thickness in the open gate area with the roughness below 0.2 nm, and the thickness of the AlGaN barrier layer can be adjusted properly. P-type doping concentrations of the GaN layer and AlGaN barrier have to be adjusted; the 2DHG has to be contacted (in the ideal case by ohmic contacts).

C. N-Face GaN/AlGaN/GaN heterostructure with the 2DEG in the top GaN layer above the AlGaN barrier layer. The top GaN layer must be recessed to 5-9 nm thickness in the open gate area with the roughness below 0.2 nm. Thickness of the AlGaN barrier can be adjusted during growth. N-type doping levels of the GaN buffer layer and the AlGaN barrier layer must be adjusted; the 2DEG has to be contacted (in the ideal case by ohmic contacts).

D. N-Face GaN/AlGaN/GaN heterostructure with the 2DHG in the GaN buffer layer below the AlGaN barrier layer. In this case, the top GaN layer may be omitted to obtain the two-layer structure. In both, the two-layer and three-layer configurations, the top GaN layer must be recessed to 1-9 nm thickness in the open gate area with the roughness below 0.2 nm, and the thickness of the AlGaN barrier can be adjusted properly.

Figure 6:
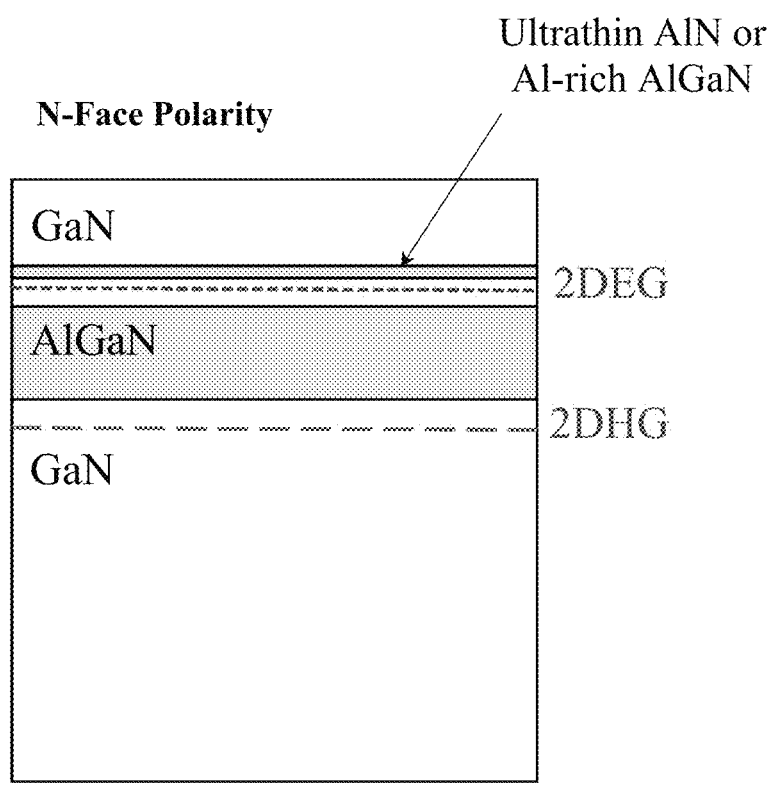
FIG. 6 schematically shows the formation of the 2DEG conducting channel in the N-face three-layer AlGaN/GaN PC-HEMT structure with an ultrathin Al(GaN)N layer for improved confinement.

In all the above structures, the deposition of a dielectric layer on top might be beneficial or even necessary to obtain a better confinement (as in case of the N-face structures). As shown in FIG. 6, for the above "C" structure, it may be even more beneficial to include an ultrathin (about 1 nm) AlN or AlGaN barrier layer with high Al-content on top of the 2DEG channel to improve the confinement.

The preferable structures of the embodiments are structures "B" and "C". In the structure "B", the 2DHG conducting channel formed in the top GaN layer, which has a higher chemical stability (particularly towards surface oxidation) than the AlGaN layer. Concerning the structure "C", the 2DEG conducting channel might be closer to the surface. Therefore, the electron mobility might be lower than in the 2DEG structure with the Ga-face polarity. In general, the polarity of the heterostructure can be adjusted by the choice of the substrate (e.g. C-face SiC) or by the growth conditions.

Another important feature of the sensor of the present application is that an electrical connection of the heterojunction structure to the 2DEG or 2DHG channel is realised via capacitive coupling to the electrical metallizations through a Schottky barrier contact. "Capacitive coupling" is defined as an energy transfer within the same electric circuit or between different electric circuits by means of displacement currents induced by existing electric fields between circuit/s nodes. In general, ohmic contacts are the contacts that follow Ohm's law, meaning that the current flowing through them is directly proportional to the voltage. Non-ohmic contacts however do not follow the same linear relationship of the Ohm's law. In other words, electric current passing through non-ohmic contacts is not linearly proportional to voltage. Instead, it gives a steep curve with an increasing gradient, since the resistance in that case increases as the electric current increases, resulting in increase of the voltage across non-ohmic contacts. This is because electrons carry more energy, and when they collide with atoms in the conducting channel, they transfer more energy creating new high-energy vibrational states, thereby increasing resistance and temperature.

When electrical metallizations are placed over single-crystalline or polycrystalline semiconductor material, the "Schottky contact" or "Schottky barrier contact" between the metal and the semiconductor occurs. Energy of this contact is covered by the Schottky-Mott rule, which predicts the energy barrier between a metal and a semiconductor to be proportional to the difference of the metal-vacuum work function and the semiconductor-vacuum electron affinity. However, this is an ideal theoretical behaviour, while in reality most interfaces between a metal and a semiconductor follow this rule only to some degree. The boundary of a semiconductor crystal abrupt by a metal creates new electron states within its band gap. These new electron states induced by a metal and their occupation push the centre of the band gap to the Fermi level. This phenomenon of shifting the centre of the band gap to the Fermi level as a result of a metal-semiconductor contact is defined as "Fermi level pinning", which differs from one semiconductor to another. If the Fermi level is energetically far from the band edge, the Schottky contact would preferably be formed. However, if the Fermi level is close to the band edge, an ohmic contact would preferably be formed. The Schottky barrier contact is a rectifying non-ohmic contact, which in reality is almost independent of the semi-conductor or metal work functions.

Thus, a non-ohmic contact allows electric current to flow only in one direction with a non-linear current-voltage curve that looks like that of a diode. On the contrary, an ohmic contact allows electric current to flow in both directions roughly equally within normal device operation range, with an almost linear current-voltage relationship that comes close to that of a resistor (hence, "ohmic").

Since the source and drain contacts are non-ohmic (i.e. capacitively-coupled), the DC readout cannot be carried out. To electrically contact the 2DEG/2DHG channel underneath, about 5-20 nm bellow the metallizations, the AC-frequency regime must be used. In other words, the AC readout or impedance measurements of the electric current flowing through the 2DEG/2DHG-channel should be performed in this particular case. The capacitive coupling of the non-ohmic metal contacts with the 2DEG/2DHG channel becomes possible only if sufficiently high AC frequency, higher than 30 kHz, is applied to the metallizations. To sum up, the electrical metallizations, which are capacitively coupled to the 2DEG/2DHG channel utilise the known phenomenon of energy transfer by displacement currents. These displacement currents are induced by existing electrical fields between the electrical metallizations and 2DEG/2DHG conducting channel operated in the AC frequency mode through the Schottky contact as explained above.

Surface acoustic wave (SAW) resonators are a class of MEMS based on the modulation of surface acoustic waves. The detection mechanism for SAW resonators utilizes changes in the amplitude, velocity, or phase of a SAW propagating along the substrate due to changes to the characteristics of the propagation path. In general, the energy of the SAW is normally concentrated in a surface region with a thickness of less than 1.5 times its wavelength. Therefore, the SAW resonator is extremely sensitive to its environment.

The principle of the inter-digitated transducer (IDT)-based SAW sensor is shown in FIGS. 7a-7c. It relies on two IDTs—one to launch and the other to detect a wave that travels from one end of the piezoelectric substrate to the other. A pair of IDTs, fabricated on the GaN/AlGaN substrate, serves as input and output ports of the signals. Fabrication of the SAW sensors comprises material selection, patterning, dicing, surface functionalisation and final packaging. The SAW sensors are fabricated from piezoelectric materials, typically quartz. Each IDT is composed of many pairs of photolithographically defined fingers, wherein each finger is only a few micrometres wide.

The SAW is extremely sensitive to tiny mass changes and capable of detecting as few as 100 picogram/cm$^2$ amount of an analyte, which corresponds to sensitivity to less than 0.01 monolayer of carbon. The velocity and the attenuation of acoustic waves result from changes in surface mass in SAW devices. Measuring both these properties simultaneously helps determine the nature and cause of the sensor response. In general, the SAW sensors are designed by choosing the desired frequency and bandwidth of operation.

The SAW can be expressed as a complex value $\gamma=\alpha+i\beta$, wherein the given or calculated attenuation constant $\alpha$ and propagation constant $\beta=2\pi/\lambda$ are important design parameters of the SAW sensor ($\lambda$ is the acoustic wavelength). Another important design parameter is the electromechanical coupling coefficient $K^2$, which is a measure of the efficiency for converting an applied microwave signal into mechanical energy. These parameters will determine the magnitude of the observed changes in the SAW phase velocity and attenuation of the SAW intensity.

As shown in FIGS. 7b-7c, the operation frequency of the SAW sensor $f_0$ can be chosen by properly choosing the inter-digital finger spacing d such that $f_0=v/d$, where v is the wave propagation velocity in the specific substrate. Consequently, the dimensions of the designed SAW sensor depend on the chosen operating frequency, which can vary from a micrometre for 1-10 GHz to millimetres for kHz-MHz operation. SAW sensors operating in the GHz range can be readily designed and easily integrated with RF, the diverse MIMIC, and the microstrip circuits for low power wireless remote sensing. The bandwidth of the acoustic wave is given by B=v/2Nd, where N is number of inter-digital fingers, as shown in FIG. 7b.

The aforementioned GaN/AlGaN-based substrates are almost ideal materials for the SAW sensors due to their high SAW propagation velocity of about 4000 m/s, high electromechanical coupling coefficients, and their compatibility with the RF electronic integration. These materials also show excellent resistance to humidity and chemical etching. The GaN/AlGaN heterostructures described above exhibit a strong piezoelectric effect and have been used to fabricate the ultra-sensitive SAW-microbalances, exploiting the influence of mass accumulation on the SAW propagation. The high electromechanical coupling coefficients of the GaN/AlGaN substrate ($K^2_{eff}$=0.001-0.002), in combination with the low acoustic loss and SAW high velocity, enable their use in high-frequency and diverse low-loss RF applications. Therefore, the GaN/AlGaN-based SAW resonators operating up to the 10 GHz range can be designed and integrated with any wireless remote sensing applications.

Thus, using the GaN/AlGaN heterostructure as the piezoelectric substrate for the SAW sensors will result in a considerable improvement of the detection limit and in a high selectivity. This is a result of the 2DEG/2DHG's sensitivity to any proximal surface charge and a high mass sensitivity, as explained above. Thus, the GaN/AlGaN hetero-structures and Schottky diodes can be integrated with a SAW sensor to create a rather unique resonant SAW tuning device with low acoustic loss, low loss RF performance and high frequency. The 2DEG/2DHG in a GaN/AlGaN structure and in a SAW propagation path interacts with the lateral electric field, resulting in ohmic loss, which attenuates and slows the SAW. This mechanism can be used to tune the SAW propagation velocity.

However, to combine the 2DEG/2DHG with the SAW achieving a maximal sensory effectiveness, some physical aspects must be taken into account. The actual functional combination of the 2DEG/2DHG with the SAW requires complete or partial removal, depletion or appropriate patterning of the 2DEG/2DHG in the quantum-well channel in the acoustic wave propagation region. The high charge conductivity in the conducting 2DEG/2DHG channel can screen the electric field and reduce the acousto-electric transductions in the IDTs.

The metallic IDTs introduce inherent mass loading effects and triple-transit-interference (TTI), reducing the signal-to-noise ratio. In conventional SAW sensors, the average SAW propagation velocity under the metallic IDTs will be reduced from the free-surface value and will result in a reduction of its centre frequency with an increased amplitude and phase rippling across the bandpass due to signal reflection from the metallic IDTs.

Figure 8:
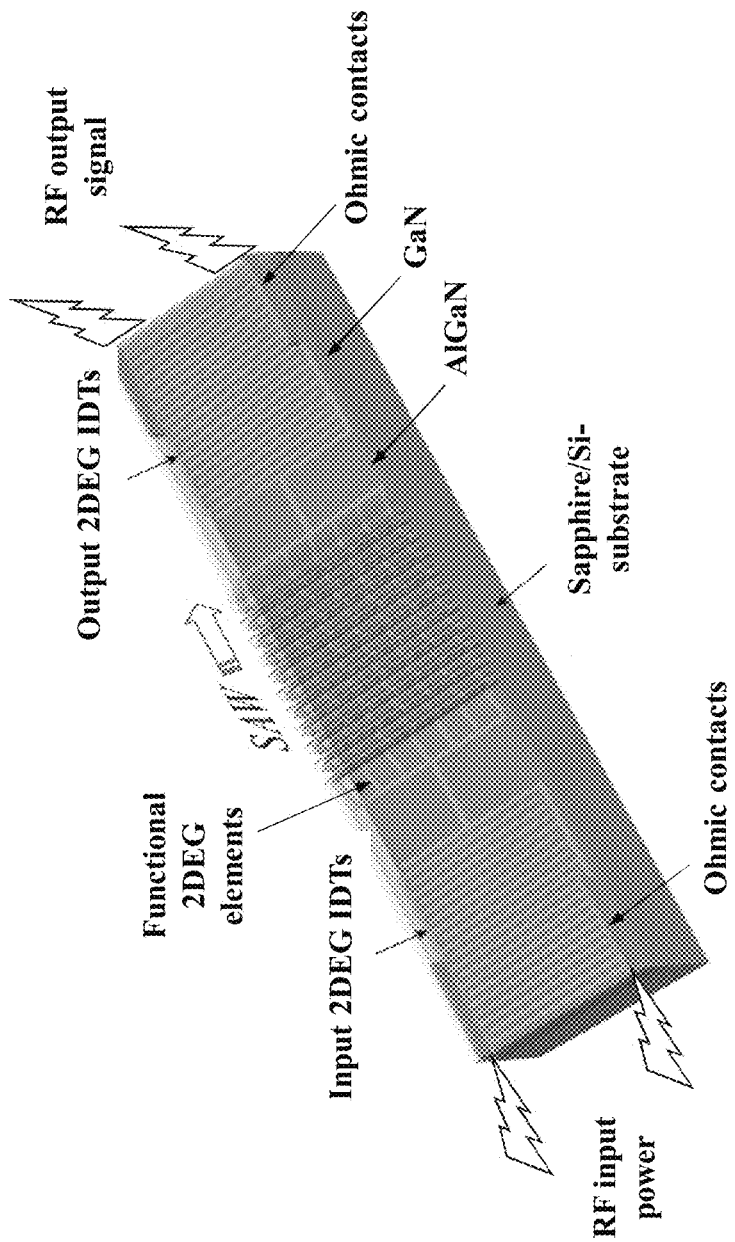
FIG. 8 schematically shows a SAW RFID sensor of an embodiment with 2DEG IDTs on a GaN/AlGaN heterostructure.

The aforementioned problems can be overcome by using the IDT fingers based on the PC-HEMT-like structures whilst also increasing the sensor sensitivity. In that case, the RF characteristics of the SAW device with planar 2DEG/2DHG IDTs are nearly equal to those using metallic IDTs with a Schottky contact. Moreover, the resulting mass-loading effects and the TTI are suppressed when using the 2DEG/2DHG-based transducers instead of the metallic IDTs. Also, the detection area of the SAW sensor or resonator can be right on top of the planar 2DEG/2DHG IDTs rather than in a separate SAW propagation area in between the IDTs. FIG. 8 schematically shows a sensor with such 2DEG/2DHG IDTs on top of a GaN/AlGaN heterostructure.

In general, when the metallic IDTs are placed on a semiconductor material, the Schottky contact is formed between the metal and the semiconductor, as explained above (regarding non-ohmic contacts). Considering the charge sensitivity mechanism in the 2DEG/2DHG-based SAW devices, other charge sensitive 2DEG/2DHG areas can be added that operate in either the resonant centre frequency or in other resonant modes. These additional patterned 2DEG/2DHG areas will further enhance the resonant changes in the main SAW sensor through their charge gating. By studying the different signal shapes for different resonant modes, a selective sensing can be introduced.

Besides the charge-sensitive 2DEG/2DHG IDTs, other functional elements based on the 2DEG/2DHG conducting channel, such as a 2DEG/2DHG-Schottky diode and a 2DEG/2DHG-planar non-symmetrical diode, nanowires and high electron mobility transistors can be placed between and connected with input and output IDTs operating in a resonant filter mode, as shown in FIG. 8. The electrical characteristics of such functional elements are modulated due to acoustoelectric transduction, which is time correlated (synchronized with IDTs). This results in a minimal electric loss and a specified signal shape for the SAW resonance. Through the electrostatic field gating, for example by redox processes occurring on the surface, this resonant SAW filter mode is easily affected (frequency, amplitude).

Thus, due to its piezoelectric nature, the GaN/AlGaN heterojunction structures can be used as SAW sensors on the free standing GaN/AlGaN membrane. It is known, that the SAW sensors are very sensitive to surface charges in the SAW propagation path between emitter and receiver finger-electrodes or IDTs. In addition, the SAW sensors have a very high Q-factor at the resonant frequency. Moreover, the SAW sensors can be easily powered by an RF field with the corresponding frequency having an appropriate meander-based antenna. The SAW sensor offers the intrinsic RFID integration by using the orthogonal frequency coding. On the other hand, the 2DEG/2DHG-based sensors increase the evanescent near-field acoustoelectric effect through the 2DEG/2DHG-density charge-responsivity following by drastic increase of sensitivity to proximal electrical charges.

The functional basic topology of the sensor of an embodiment is schematically shown in FIGS. 9a and 9b. The aim of the 2DEG/2DHG-SAW sensor topology is to achieve the largest possible effect of the SAW-transducer S21-transfer parameter without sacrificing the sensor stability. Lines (100) in FIGS. 9a and 9b are assigned to the metal IDT structures, band (102) stands for a PC-HEMT-like structure, which is actually a 2DEG/2DHG structure recessed to the thickness of 5-9 nm to achieve the pseudo-conducting effect, and area (103) shows the GaN/AlGaN piezoelectric substrate growing optionally on free-standing membranes (101).

Thus, in one aspect, the SAW RFID sensor chip of the present application comprises:

a piezoelectric substrate (103) optionally growing on free standing membranes (101), said substrate comprising a piezoelectric layer and a multilayer heterojunction structure, said structure being made of III-V single-crystalline or polycrystalline semi-conductor materials, deposited on said piezoelectric layer and comprising at least one buffer layer and at least one barrier layer, said layers being stacked alternately;

at least one pair of metal interdigitated transducers (IDT) (100) mounted on said piezoelectric substrate (103), for receiving a radio frequency (RF) input signal, transducing said input signal into a surface acoustic wave (SAW), propagating said surface acoustic wave along a surface of said piezoelectric substrate (103) and transducing said propagated surface acoustic wave into an output RF signal;

at least one PC-HEMT-like structure (102) deposited on said piezoelectric substrate (103) for forming the pseudo-conducting 2DEG or 2DHG channel in said heterojunction structure at the interface between said buffer layer and said barrier layer; and electrical metallizations (not shown in the figure) capacitively-coupled to said IDTs (100) and to said PC-HEMT-like structures (102) for inducing displacement currents, thereby creating non-ohmic source and drain contacts, for connecting said sensor chip to an electric circuit.

Using this configuration with the free-standing membranes makes it possible to increase selectivity of the sensor via adding mechanical stress (mass loading effect) as an additional parameter of the sensor. The very flexible free-standing substrate columns-like membranes (101) can be made of the same material as the piezoelectric substrate layer (103) in all configurations of the sensor. In a particular embodiment, the free-standing membranes (101) are grown, for example, from sapphire, silicon, silicon carbide, gallium nitride or aluminium nitride, preferably gallium nitride (GaN), having thickness of 0.5-2 µm. As an example, the free-standing substrate membranes show high sensitivity to any tensile/compressive/mechanical stress changes on the surface of the multilayer heterojunction structure. This results in a mass loading effect, which will be discussed below.

In general, mechanical sensors, much like pressure sensors, are based on the measurement of the externally induced strain in the heterostructures. The pyroelectric properties of group-III-nitrides, such as gallium nitride (GaN), allow two mechanisms for strain transduction: piezoelectric and piezoresistive. The direct piezoelectric effect is used for dynamical pressure sensing. For measurements of static pressure, such sensors are not suitable due to some leakage of electric charges under the constant conditions. For static operation, the piezoresistive transduction is more preferable.

Piezoresistive sensors using wide band gap materials have been previously employed using hexagonal silicon carbide bulk materials for high temperature operation. A piezoresistivity of GaN and AlGaN structures is comparable to silicon carbide. However, the piezoresistivity can be further amplified by any HEMT structure, as taught by Eickhoff et al (2001) in "*Piezoresistivity of AlxGa1-xN layers and AlxGa1-xN/GaN heterostructures*", Journal of Applied Physics, 2001, 90(7), 3383-3386. For piezoresistive strain sensing at relatively lower pressures (or pressure differences), diaphragm or membranes should be used, where the external pressure is transferred into a changed internal strain caused by bending, as shown in FIG. 9c. The resulting change in polarization alters the 2DEG/2DHG channel current which is measured.

Eickhoff et al (2001) conducted the first experiments on AlGaN/GaN hetero-structures where the 2DEG channel confined between the upper GaN and AlGaN barrier layer and demonstrated the linear dependence of the 2DEG channel resistivity on the applied strain. Moreover a direct comparison to cubic SiC and a single AlGaN layer clearly demonstrated the superior piezoresistive properties of the latter. From these results, it is clear that the interaction of piezoelectric and piezoresistive properties improves the sensitivity of pressure sensors by using GaN/AlGaN hetero-structures confined with the 2DEG channel.

The sensor configuration schematically shown in FIGS. 9a and 9b involves piezoelectrically coupled, charge and mass sensitive, free-standing GaN membranes, which are prepared, for example, according to U.S. Pat. No. 8,313,968, and offer an elegant and effective solution to achieve both downscaling and an integrated all-electrical low-power sensing-actuation. As mentioned above, GaN exhibits both, piezo- and pyro-electrical properties, which can be functionally combined. Whereas the piezoelectricity enables realisation of an integrated coupling mechanism, the 2DEG/2DHG additionally delivers a pronounced sensitivity to mechanical stress and charge, which allows the sensor to use the pyroelectric effects. The dynamic change in 2DEG/2DHG conductivity is also caused by a change in piezoelectric polarisation.

Figure 10B:
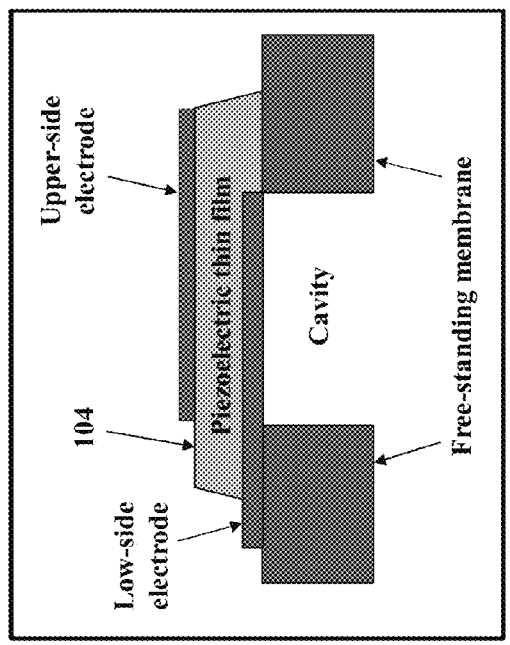
FIGS. 10a-10b schematically show a basic topography of the 2DEG-FBAR-SAW sensor configuration of an embodiment with a thin resonating film (104) on top of the substrate.
Figure 10A:
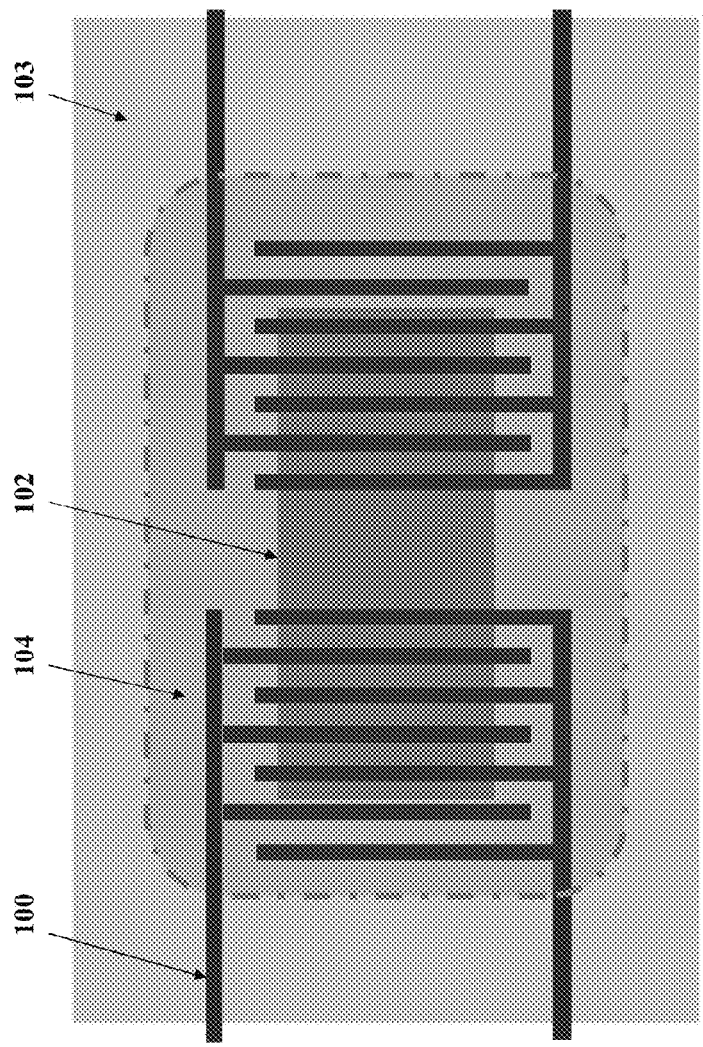

FIGS. 10a and 10b show another configuration, which is very similar to the configuration shown in FIG. 9a-9b discussed above. However, here a resonating piezoelectric ultrathin film (104) is introduced on top of the substrate (103). A bulk wave propagating inside the piezoelectric ultrathin film (104) is generated by putting it between two electrodes and applying a high frequency signal. The wave resonates at a particular frequency according to the thickness of the ultrathin film. Such resonator is called a Film Bulk Acoustic Resonator (FBAR), and it is combined in the sensor of an embodiment with the PC-HEMT-like structure (102) for achieving maximum sensitivity. The FBAR traditionally uses aluminium nitride (AlN) as its piezoelectric material, however other group-III-nitrides can be a possible alternative.

In general, the structures of FBARs are made by forming cavities with a dry-etching machine called a "Deep-RIE" from the reverse side of the substrate or by using a sacrifice layer, forming the sacrifice layer under the lower electrode, a piezoelectric thin film and upper electrode, then removing the layer to make a space beneath the lower electrode.

The low-side and upper-side electrodes shown in FIG. 10b are designed with so-called "leaky waves" having acoustic wave velocities of around 4000 m/s. "Leaky waves" can be defined as propagating waves that concentrate most of the energy close to the surface of the substrate, but have some radiation of bulk waves into the substrate while propagating. The piezoelectric substrate used for forming leaky waves is normally made of a LiTaO$_3$ single crystal having X, Y and Z axes and a cut plane. The X axis of the crystal is oriented in a direction of the SAW propagation, while the cut plane of the crystal is rotated around the X axis at a certain angle of rotation with respect to the Y axis towards the Z axis. This angle normally ranges between 40° and 42°. That is why the substrate is commercially named "42° Y—X LiTaO$_3$". The IDTs (100) are formed on the substrate and aligned in a row in the direction of the SAW propagation, as shown in FIG. 10a.

Each IDT has a pair of mutually opposed primary electrode fingers (shown as lines (100) in FIGS. 10 and 11) and secondary electrode fingers (shown in FIG. 9) and includes at least one front transducer, one middle transducer and one rear transducer, which are aligned in the row in the direction of the SAW propagation, as shown in FIG. 10a.

FIG. 11 shows the photolithographic layout masks of the 2DEG-based SAW resonator using the standard configuration with two symmetrical IDT structures (fingers). The IDT fingers are preferably made of Cr10/60Au metal alloys and have a preferable width of 200, 300, 400, 500 or 700 nm. They are fabricated in one e-beam step as a lift-off bi-layer resist system stack or a negative resist and ion milling. The 2DEG/2DHG is not structured in that case and interacts with the surrounding medium. The area (601) in the middle represents the primary IDT fingers on a free-standing area, where the (silicone) substrate will be removed by the deep reactive-ion etching (DRIE) process, as mentioned above.

Figure 12:
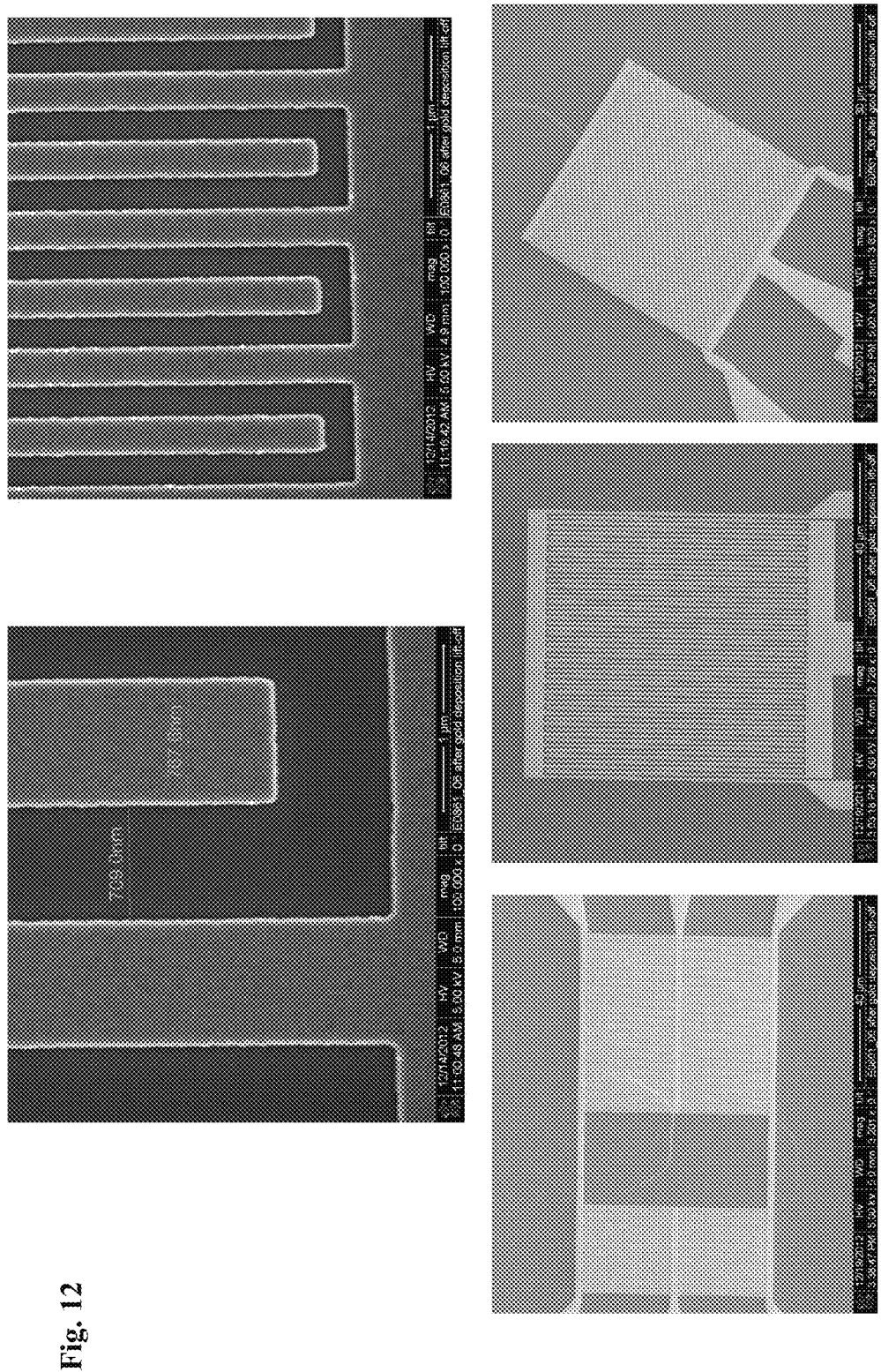
FIG. 12 shows the SEM images from several different IDT layouts of the SAW resonators fabricated via the lift-off/or ion-milling patterning technique.

FIG. 12 shows the SEM images of the SAW resonator of an embodiment as shown in FIGS. 9-11. This SAW resonator is fabricated via the lift-off/or ion-milling patterning technique. FIG. 13 shows the microscope images of these SAW resonators on the free-standing GaN/AlGaN membranes having the unstructured 2DEG/2DHG area with the silicon substrate removed via the DRIE process. The SAW IDTs shown here have different IDT periods ranging from 200 nm to 700 nm and hence, reflect light differently. In general, leaky waves are frequently used in these kinds of substrates for their relatively large electromechanical coupling coefficient, which enables them to form a relatively wide passband required for transmitting and receiving mobile device signals. For example, in the present SAW resonator having a working frequency of 2 GHz, the wavelength $\lambda$ is calculated from $\lambda \times 2 \times 10^9 = 4000$ m/s, resulting in $\lambda = 2$ μm. This calculated wavelength should be equal to the length twice as the electrode pitch for excitation, and assuming that the spaces between the electrodes are the same as the electrode width, the width of the electrode is estimated to be 0.5 μm. The actual spaces between the electrodes are about 0.7 μm as seen in FIG. 12.

Thus, the IDT structures (100) receive the RF signal of about 0.5-2.5 GHz and exhibit the piezoelectric effect creating acoustic waves over the surface of the resonator. These surface acoustic waves propagate along the substrate with constructive interference from both input and output IDTs. As shown in FIGS. 9-10, the PC-HEMT-like structure (102) is placed in the SAW bidirectional propagation path and also patterned in such a manner as to electrically shortcut the positive and negative electric charges from running the SAW and to thereby considerably change or minimize the amplitude of the signal which is received on both IDTs via the direct piezoelectric effect. The SAW itself is generated by zero-power meander antenna (not shown here) connected to both IDTs (100).

In the above sensor configuration of an embodiment, shown in FIGS. 9-10, the piezoelectric substrate (103) comprises a suitable material for forming the barrier layer and is composed, for example, of sapphire, silicon, silicon carbide, gallium nitride or aluminium nitride. The heterojunction structure made of GaN/AlGaN is deposited on this piezoelectric substrate layer, for example, by a method of metalorganic chemical vapour deposition (MOCVD). The PC-HEMT-like structure (102) is created in a close proximity to the interface between the GaN buffer layer and the AlGaN barrier layer. The specific thickness of 5-9 nm of the AlGaN barrier layer is achieved by either dry etching the semiconductor material of the layer, i.e. recessing layer in the open gate area with the etching rate of 1 nm per 1-2 min in a controllable process, or coating the AlGaN buffer layer with an ultrathin layer of the AlGaN semiconductor material. In order to increase the charge sensitivity of the sensor, the surface of the recessed ultrathin AlGaN layer is post-treated with the plasma (chloride) epi-etch process. Consequently, the natively passivated surface is activated by the plasma etch to create an uncompensated (i.e. ionised) surface energy bonds or states, which are neutralized after the MOCVD growing.

The barrier layer then may be either recessed or grown as a thin layer to get the pseudo-conducting 2DEG/2DHG channel, which is formed at the interface between the buffer GaN layer and the barrier AlGaN layer, as described above in detail. The recessed GaN/AlGaN structure is actually a PC-HEMT-like structure (because of its specific thickness) resulting in a pseudo-conducting current in the 2DEG/2DHG channel. As explained above, this channel formed at the interface between the buffer GaN layer and the barrier AlGaN layer serves as a main sensitive element of the sensor reacting to a surface charge and potential. The formed 2DEG/2DHG channel is configured to interact with very small variations in surface or proximal charge or changes of electrical field as a result of the propagating surface acoustic weaves creating a piezoelectric effect, and thereby, interacting with the donor-like surface trap states of the AlGaN barrier layer.

Figure 14:
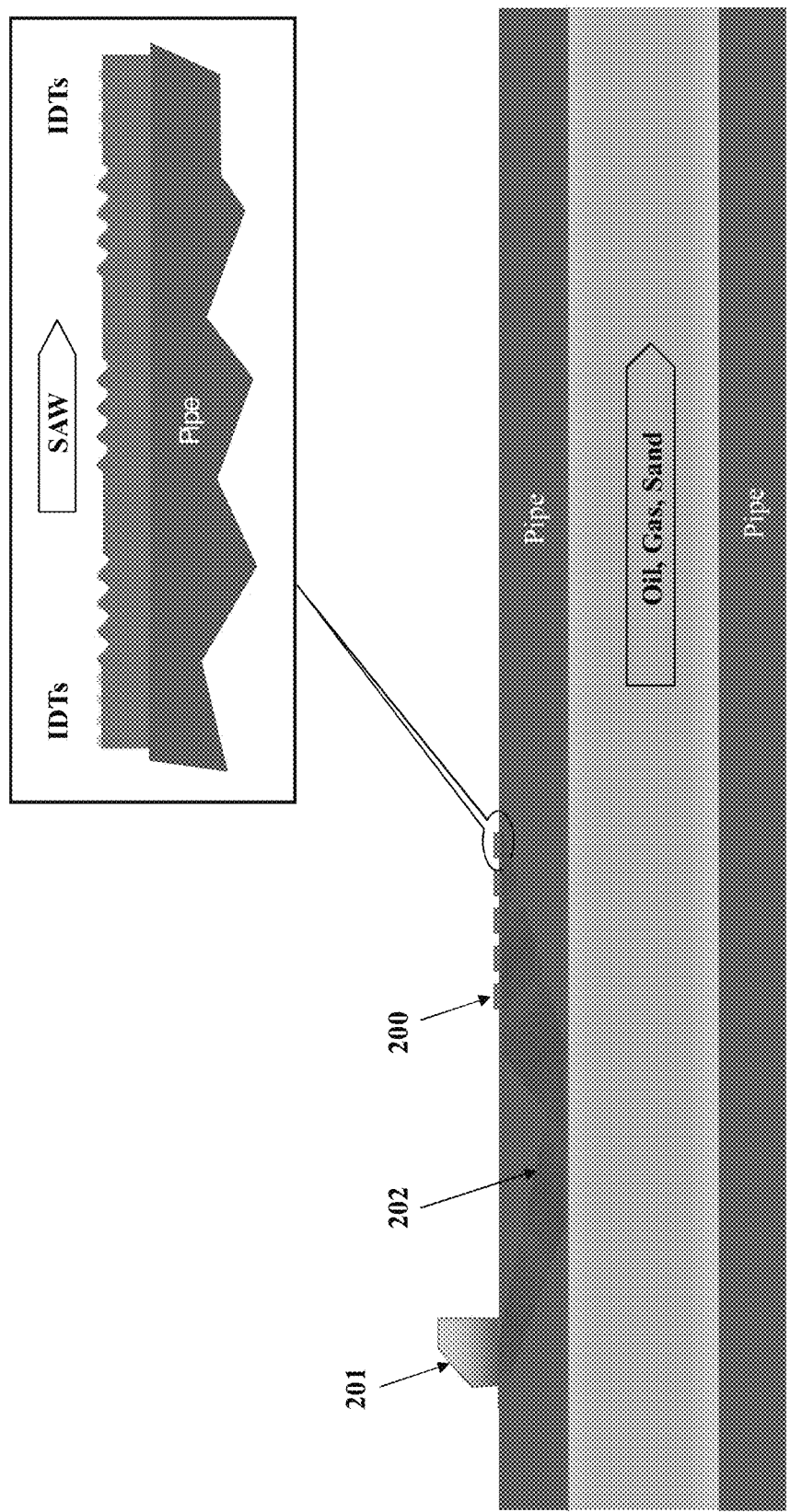
FIG. 14 schematically shows a method for non-destructive detection of the pipe content and monitoring the structural pipe material health with an ultrasensitive microphone of an embodiment.

FIG. 14 schematically shows a method for non-destructive detection of the pipe content (for example, oil, gas or sand) and monitoring the structural pipe material health using an ultrasensitive microphone (200) or microphones array of an embodiment. The microphone (200) is actually a 2DEG-FBAR-SAW sensor (enlarged in the layout) of the embodiment. The method comprises the following steps:
1) Placing the ultrasound emitter actuator (201) directly on the pipe;
2) Placing the microphones (200) either in a circle around the ultrasound emitter actuator (201) or laterally shifted along the pipe (as in FIG. 14); and
3) Detection or monitoring of the reflected ultrasound wave front (202) either with a single microphone (200) or with the microphones array (as in FIG. 14).

Figure 15B:
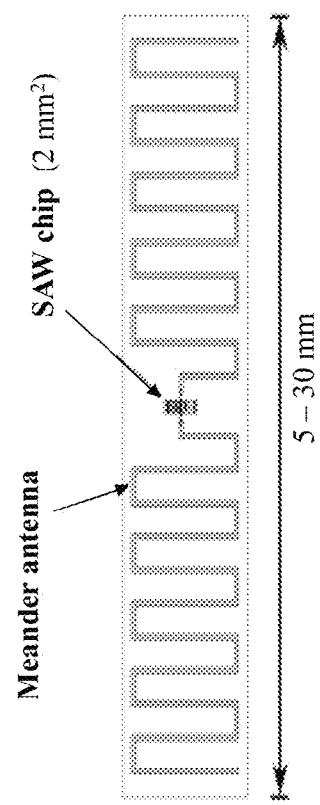
FIG. 15b schematically shows a sensor of an embodiment comprising the SAW resonator chip and the meander antenna generating the SAW on the chip surface.
Figure 15A:
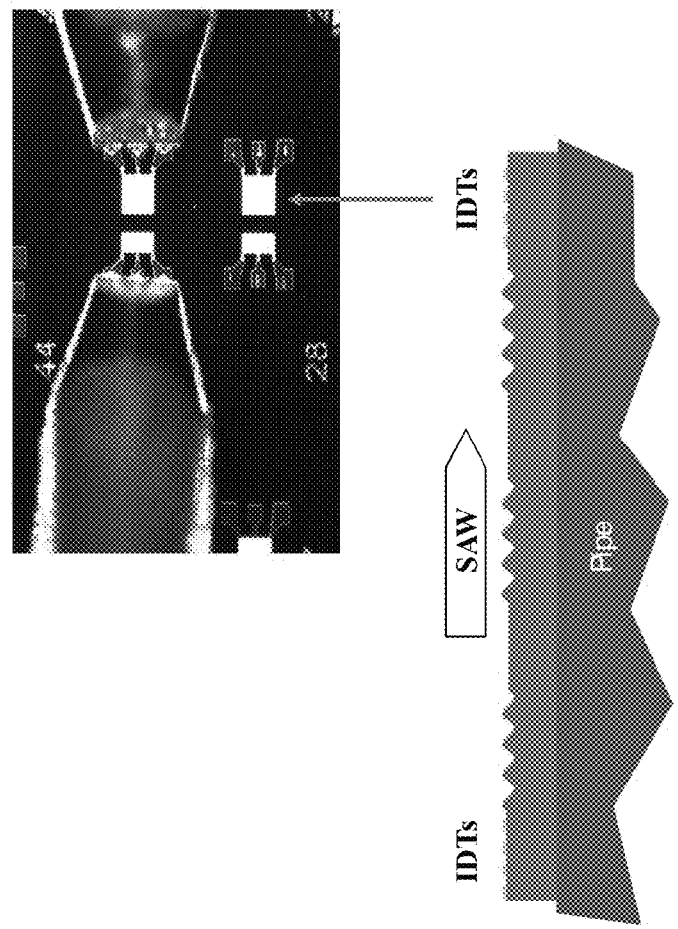
FIG. 15a shows a microscope image of the ultrasensitive microphone of an embodiment.

The microphones array creates a passive phase array configuration allowing considerably more accurate and selective detection of the chemical content in the pipe. A microscope image of the ultrasensitive microphone of the present application built by the present inventors is shown in FIG. 15a. It is actually a SAW resonator chip, as described above, incorporating the PC-HEMT-like structure for increasing sensitivity of the sensor. The SAW itself is generated by a zero-power meander antenna shown in FIG.

15b. The sensor with the meander antenna has dimensions of 5-30 mm (length)×1-5 mm (width), while the SAW resonator chip is about 2 mm$^2$. The SAW resonator chip has a direct mechanical contact with a material to be sensed, such as an outer wall of the pipe. The detection and monitoring of the pipe content, which is usually water, oil, sand or gas, is based on the ultrasound wave front reflection from the metal wall or content of the pipe at the interface between the wall and the content.

Amplitude of the reflected ultrasound signal is very low due to a very high initial ultrasound wave coupling and multiple secondary ultrasound wave reflections lose. In general, the amplitude, shape, phase and Doppler shift of the ultrasound wave front reflected at the interface between the pipe wall and the pipe content is mostly depending on density, pressure, composition and speed of the content flow inside the pipe. A single microphone of the present application is extremely sensitive to the ultrasound wave energy interacting with a highly pyroelectric GaN/AlGaN heterojunction. The highest sensitivity of the microphone can be reached only at the resonant frequencies of this microphone. The higher the resonance frequency, the lower is the detection limit and higher is sensitivity. In order to achieve the resonant frequencies, the present inventors proposed to use the hybrid FBAR-SAW on the free-standing GaN/AlGaN membranes transducing the SAW waves, as described above, and having the first harmonic resonant frequency with high amplitude compared to non-free standing structures. These new prototype FBAR-SAW resonators of FIG. 13 designed and built by the inventors are shown in FIG. 16 together with the schematic drawing of the FBAR-SAW resonator based on the free-standing membranes placed in contact with the pipe being sensed.

Each ultrasensitive microphone (200) shown in FIG. 14 may be RFID-coded, have a zero-power NFC capability and further be equipped with a bidirectional receiver-emitter antenna structure. It is also possible to couple all the microphones to a single meander antenna and separate the mixed RFID-patterned signals by orthogonal frequency coded (OFC) from individual microphones by an algorithm, which will be disclosed elsewhere. This will allow building a zero-power SAW-sensor array without batteries and cable connections, thereby drastically reducing the sensor cost. Each SAW microphone can be further phase controlled and can detect the smallest phase change of the SAW. By operating the sensors in a phased array configuration, it will be possible to measure, for example, flow rate, liquid laminarity and gas fractions.

Figure 17:
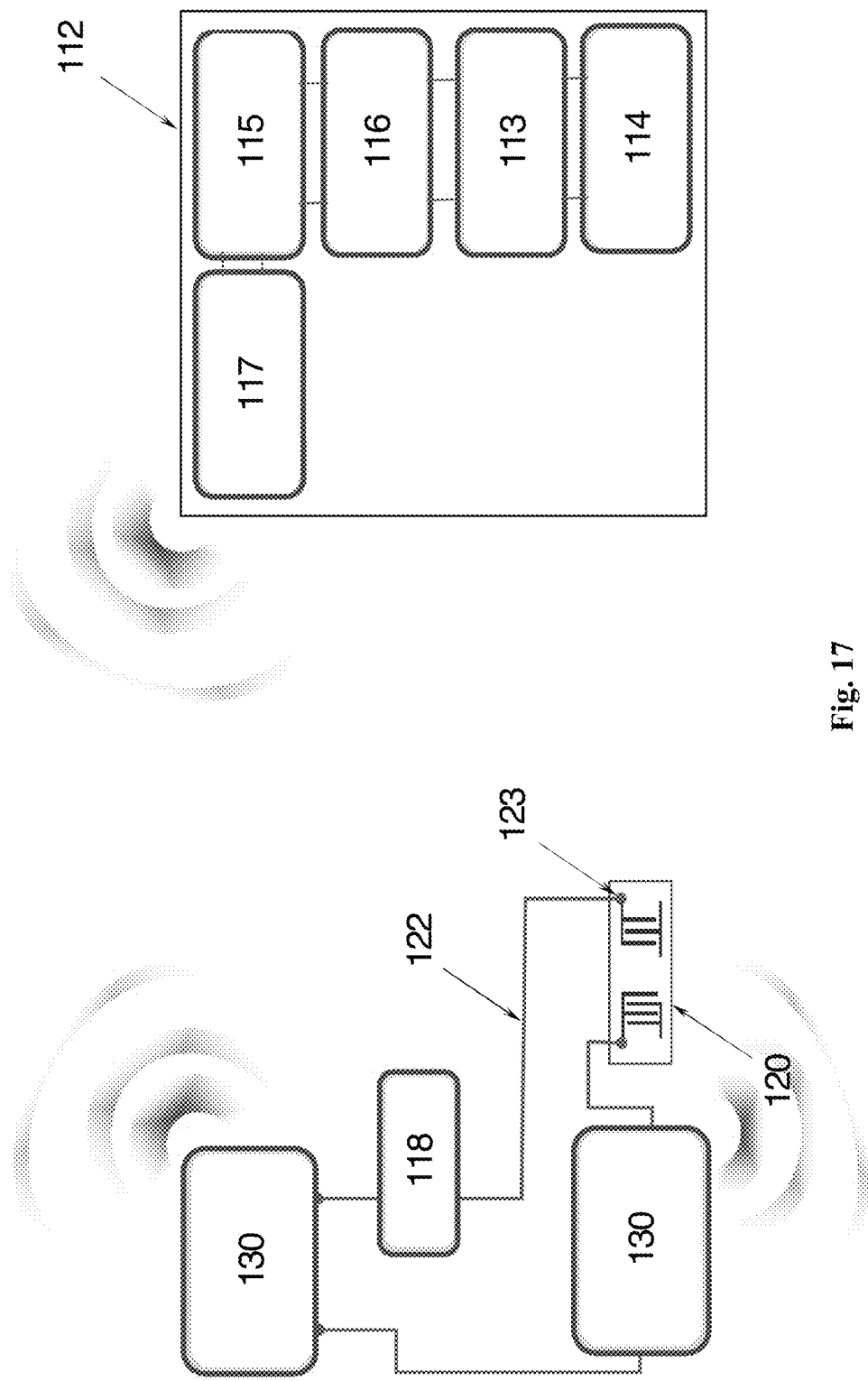
FIG. 17 schematically shows a zero-power SAW RFID sensor of an embodiment for material and structure sensing with a remote readout.

FIG. 17 schematically shows an ultrasensitive microphone of an embodiment, for material and structure sensing, with a remote readout, comprising the following components:
the SAW sensor chip (120) of the application connected via contacts (123) to an electric circuit (122);
one or two out-input SAW-RFID zero-power fractal antennas (130), each connected to said contacts (123) via the electric circuit (122) for receiving or transmitting a signal;
an output-input separation by delay line SAW transducer (118);
an integrated circuit (112) for storing and processing said signal, and for modulating and demodulating a radio-frequency (RF) signals, said circuit comprising:
a) a voltage source (114) supplying electric current to said SAW sensor chip (120) and to said one or two antennas (130);
b) an integrated or CMOS current amplifier (115) for amplification of an electric current obtained from said SAW sensor chip (120);
c) an analogue-to-digital converter (ADC) with wireless input/output modules (116) connected to said current amplifier (115) for wireless outputting the converted signal to a user interface or external memory;
d) a microcontroller unit (MCU) (113) for processing and converting the received signal into data readable in said user interface or external memory; and
e) a wireless connection module (117) for wireless connection of said sensor to said user interface or external memory.

The voltage source (114) can be any suitable and commercially available battery of the Li-ion type, any energy harvester with AC-DC or DC-DC converters or photovoltaic element. The ADC card (116) is any suitable analogue-to-digital converter data logger card that can be purchased, for example, from National Instruments® or LabJack®. The current amplifier (115) is connected in-line and can be any commercially available femtoampere amplifier, for example SRS® SR570, DLPVA-100-F-S, FEMTO® current amplifier DDPCA-300 or Texas Instruments® INA826EVM. Optionally, a current amplifier can be operated directly with current flowing via the 2DEG/2DHG channel of the 2DEG/2DHG structures into the amplifier with small input resistance of 1MΩ at gain higher than 10$^4$ and only 1Ω at gains lower than 200. This setup may directly amplify the electric current modulation in the 2DEG/2DHG channel originated from an external body charges. All readout components are battery powered to avoid ground loop parasitic current.

In a specific embodiment, the wireless connection module (117) can be a short-range Bluetooth® or NFC providing wireless communication between the wearable device or gadget and a smartphone for up to 20 m. If this module is Wi-Fi, the connection can be established with a network for up to 200 nm, while GSM allows the worldwide communication to a cloud. The external memory may be a mobile device (such as a smartphone), desktop computer, server, remote storage, internet storage or material diagnostics cloud.

As shown in the present application, the sensors of the embodiments are used as ultrasensitive portable microphones for material and structure sensing. The portable sensor of an embodiment should have a very small power consumption saving the battery life for a prolong usage. In this case, the non-ohmic high-resistive contacts capacitively connecting the sensor to an electric circuit are preferable. In fact, the non-ohmic contacts are capable of limiting an electric current flowing through the 2DEG/2DHG conducting channel by having an electrical resistance 3-4 times higher than the electrical resistance of the 2DEG/2DHG-channel, thereby reducing electrical power consumption without sacrificing sensitivity and functionality of the sensor. Thus, the use of the non-ohmic contacts in the sensor of the embodiments is a hardware solution allowing minimising the power consumption of the device. In another embodiment, the power consumption of the device can be minimised using a software algorithm managing the necessary recording time of the sensor and a battery saver mode, which limits the background data and switches the wireless connection only when it is needed.

As described above, the sensor of the present application can be realised in two configurations: with and without free-standing membranes. In the first configuration, the piezoelectric substrate is optionally placed on a GaN/AlGaN free-standing membrane resulting in a FBAR-SAW configuration, for achieving ultra-sensitivity. In another configuration, the sensor is based on a regular silicon piezoelectric substrate firmly connected to a structural material, such as metal pipe, being tested. In case of any stress or mechanical deformation of this structural material, the piezoelectric GaN/AlGaN stack will be also stressed or deformed, thereby changing the SAW propagation parameters. This is because of the piezoelectric polarization effect within the SAW structures resulting in change of the S21 transfer parameter on the IDT receiver.

Alternatively, the sensor of an embodiment, may be based on a piezoelectric electro-optical crystal transducer (EOC) combined with the PC-HEMT-like structure (recessed 2DEG/2DHG-based structure). The sensor based on the EOC piezoelectric substrate exhibits the highest coupling between electrical and mechanical energy compared to all other varieties of substrates. Additionally, such a substrate also has the advantages of having a high velocity-shift coefficient and a very high electromechanical coupling coefficient, K2, which yields a greater mass sensitivity in comparison with the same regular SAW device on any other piezoelectric substrates. The EOC may be any suitable electro-optical crystalline material such as $LiNbO_3$, which is brought into a physical contact with a single point on a user's body. The EOC is then illuminated with a polarised light.

In case of the $LiNbO_3$ crystalline material, the wavelength of the polarised light is about 400-600 nm. Modulated light from the light source illuminates the EOC, and then falls on the 2DEG/2DHG-based structure. The 2DEG/2DHG-based structure is ultrasensitive to an incident light creating the p-n-pairs in the AlGaN barrier layer, thereby strongly affecting the 2DEG/2DHG-channel conductivity. In general, irradiation of the 2DEG/2DHG-based structure with light switches the 2DEG/2DHG-channel from normally-off to a pseudo-conducting or normally-on state. Therefore, by contact with a body, the EOC is capable of changing its light absorbance strongly affecting the electrical current flow in the 2DEG/2DHG channel, thereby resolving any smallest light intensity changes coming from the EOC transducer. Depending on the excitation light wavelength, the position of the sensor relative to the incident light beam can be changed. For instance, in case of IR light (700-1500 nm), the sensor should be placed perpendicularly to the light beam for achieving the highest sensitivity. The parasitic charging of the EOC is compensated via the electrodes attached to the crystal. Additionally a variety of light filters in front of the sensor can be utilised.

Figure 18:
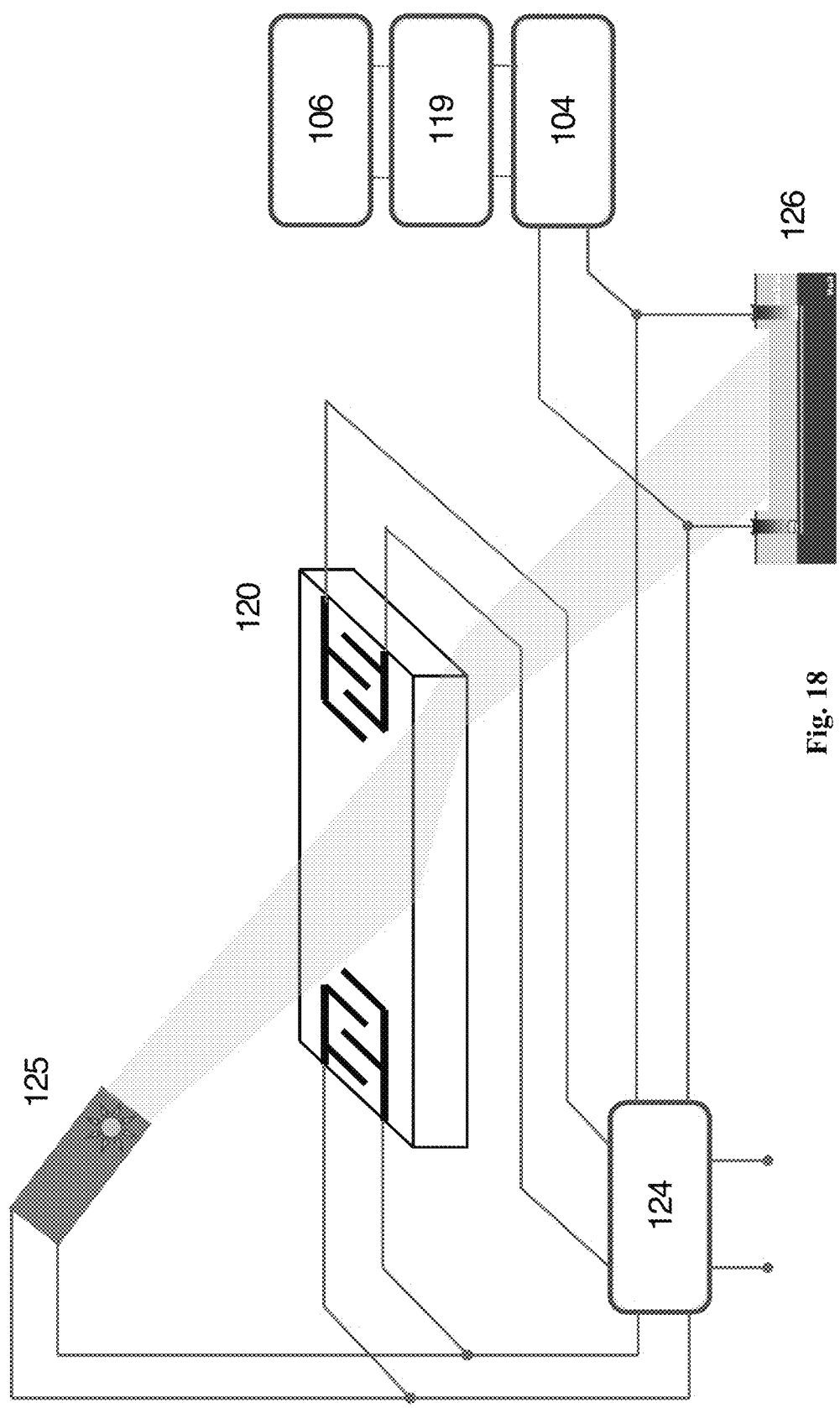
FIG. 18 schematically shows an optoelectronic sensor of an embodiment for material and structure sensing with a remote readout.

In still another embodiment, FIG. 18 schematically shows an optoelectronic sensing device of an embodiment, for material and structure sensing, with a remote readout comprising the following components:
- the SAW sensor chip (120) of the application connected to an electric circuit;
- a modulated light source (125), such as a surface-mounted-device light-emitting diode (SMD LED) or UV-VIS-IR laser diode, for irradiating the AlGaN barrier layer surface of the pseudo-conducting 2DEG/2DHG structure (126) on the sensor chip;
- optocoupler switches (124) for coupling said modulated light source (125) with said pseudo-conducting 2DEG/2DHG structure (126) on the sensor chip;
- a voltage source (104) connected to said electrical circuit for supplying electric current to said SAW sensor chip (120);
- a lock-in amplifier (119) connected to said voltage source (104) for amplification of a signal with a known carrier wave obtained from said SAW sensor chip and increasing the signal-to-noise ratio; and
- an analogue-to-digital converter (ADC) with in-built digital input/output card (106) connected to said lock-in amplifier (119) for outputting the converted signal to a user interface or external memory.

Thus, the use of the SAW-EOC configuration makes it possible to drastically increase the sensitivity of the sensor to an electrical charge, to discharge the EOC via the SAW-based charge transport along the crystal surface, to efficiently modulate polarised light from the light source and to control the SAW delay line effect with the phase velocity signal. The optocoupler switches (124) couples the 2DEG/2DHG-based structure (126) with the SAW-EOC such that the initial SAW actuation signals at the IDT emitter (left) electrodes are synchronised with the modulated light source (125) and with the $V_{DS}$ at the pseudo-conducting 2DEG/2DHG-based structure. A signal at the IDT receiver (right) electrodes is coupled back to the $V_{DS}$ via the opto-coupler (124), which is brought into a resonance with initial signals and with the light source (125) modulation. Due to a physical galvanic connection of the SAW-EOC with the body single point by spatially patterned electrodes, the EOC changes its light absorption and modulation properties. This strongly affects the resonant mode of the five initial signal sources ($V_{DS}$, emitter IDT, light source, receiver IDT and SAW-modulated light source). Thus, because of the light source-based interaction, the resonant system becomes very stable and also very sensitive to external charges.

Figure 19:
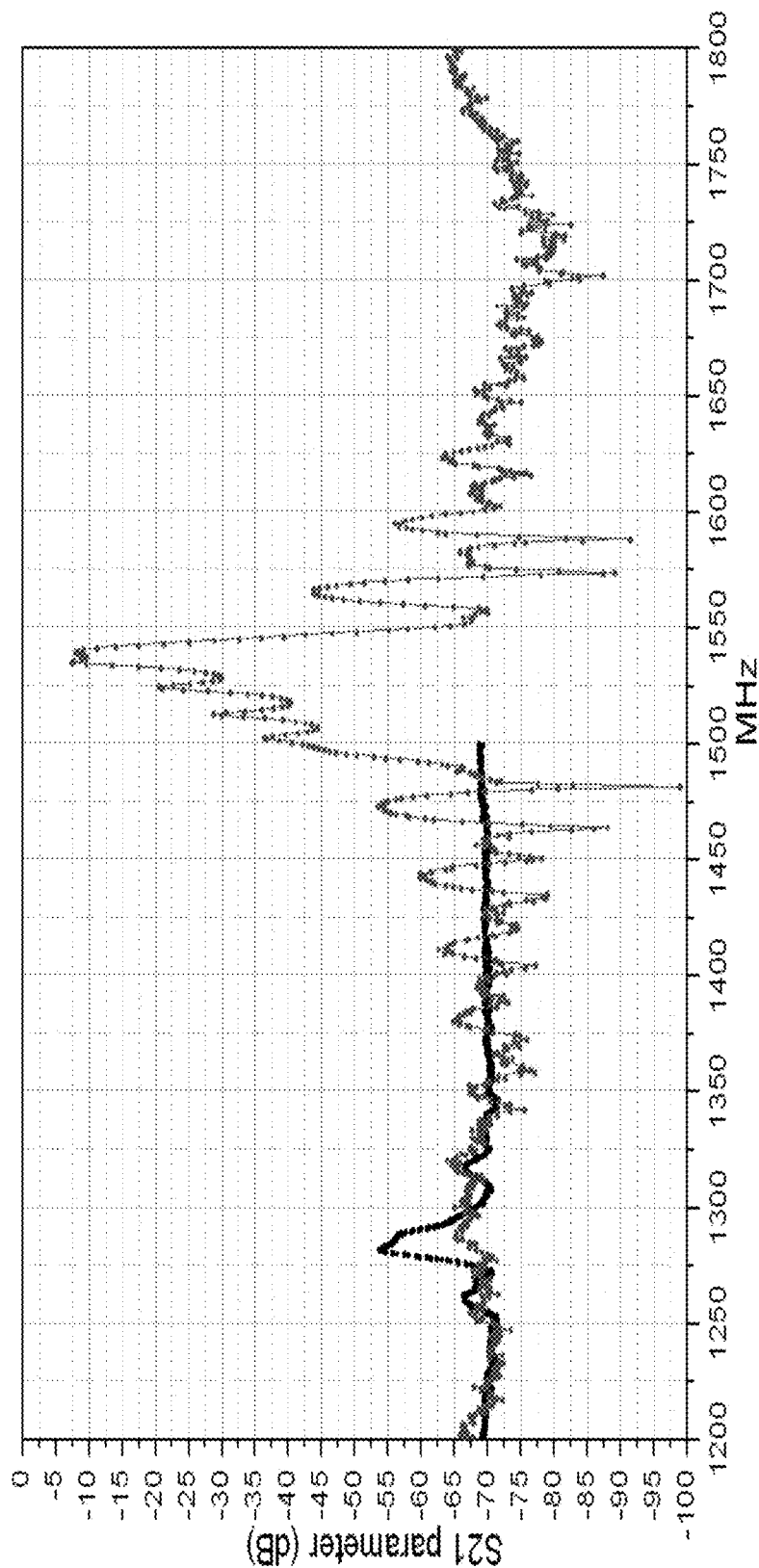
FIG. 19 shows the experimental S21-transfer parameter measured with the ultrasensitive microphone of an embodiment.

FIG. 19 shows the experimental S21-transfer parameter measured with the ultrasensitive microphone of the embodiments. In some embodiments, a method for material and structure sensing comprises the following steps:
1) Applying the sensing device of the embodiments to a material or structure to be sensed;
2) Recording signals received from the material or structure in a form of a S21-transfer parameter dynamics of the device over time (defined as S21-transfer dynamics) with said device;
3) Transmitting the recorded signals from said device to the external memory for further processing; and
4) Converting the transmitted signals to digital signals and processing the digital signals in the external memory, correlating said S21-transfer dynamics with pre-calibrated material or structure waveforms stored in the external memory, and extracting the material or structure information from said waveforms in a form of readable data.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

REFERENCES

S. D. Burnham, K. Boutros, P. Hashimoto, C. Butler, D. W. S. Wong, M. Hu, and M. Micovic, "*Gate-recessed normally-off GaN-on-Si HEMT using a new $O_2$-$BCl_3$ digital etching technique*", Phys. Status Solidi C, vol. 7, no. 7-8, pp. 2010-2012, 2010.

C. Y. Chang, S. J. Pearton, C. F. Lo, F. Ren, I. I. Kravchenko, A. M. Dabiran, A. M. Wowchak, B. Cui, and P. P. Chow, "Development of enhancement mode AlN/GaN high electron mobility transistors", Appl. Phys. Lett., vol. 94, no. 26, p. 263505, 2009.

H. Chen, M. Wang, and K. J. Chen, "Self-aligned enhancement-mode *AlGaN/GaN HEMTs using 25 keV fluorine ion implantation*", in Device Research Conference (DRC), 2010, pp. 137-138.

M. Eickhoff, O. Ambacher, "*Piezoresistivity of $Al_xGa_1$-xN layers and $Al_xGa_1$-xN/GaN heterostructures*", Journal of Applied Physics 90, 3383 (2001).

The invention claimed is:

1. A surface acoustic wave (SAW) radio-frequency identification (RFID) sensor chip comprising:
    (a) a piezoelectric substrate, said substrate comprising:
        a piezoelectric layer, and
        a multilayer heterojunction structure, said structure being made of III-V single-crystalline or polycrystalline semiconductor layers, deposited on said piezoelectric layer and comprising at least one buffer layer and at least one barrier layer, said layers being stacked alternately;
    (b) at least one pair of metal interdigitated transducers (IDT) mounted on said piezoelectric substrate, for receiving a radio frequency (RF) input signal, transducing said input signal into a surface acoustic wave (SAW), propagating said surface acoustic wave along a surface of said piezoelectric substrate and transducing said propagated surface acoustic wave into an output RF signal;
    (c) at least one pseudo-conducting two-dimensional electron gas (2DEG) or two-dimensional hole gas (2DHG) structure deposited on said piezoelectric substrate for forming the pseudo-conducting 2DEG or 2DHG channel in said heterojunction structure at the interface between said buffer layer and said barrier layer; and
    (d) electrical metallizations capacitively-coupled to said IDTs and to said pseudoconducting 2DEG or 2DHG structures for inducing displacement currents, thereby creating non-ohmic source and drain contacts, for connecting said sensor chip to an electric circuit
    characterised in that:
    (i) said III-V single-crystalline or polycrystalline semiconductor materials are GaN/AlGaN; and
    (ii) said pseudo-conducting 2DEG or 2DHG structure is a semiconducting structure formed on said piezoelectric substrate by recessing or growing a top layer of said multilayer heterojunction structure to a thickness of 5-9 nm with a surface roughness of the recessed or grown top layer being 0.2 nm or less, thereby forming the pseudo-conducting 2DEG or 2DHG channel capable of conducting electric current in the current range between normally-on and normally-off operation modes of the channel.

2. The SAW RFID sensor chip of claim 1, wherein said piezoelectric substrate is placed on a free-standing membrane.

3. The SAW RFID sensor chip of claim 2, wherein said free-standing membrane is made of sapphire, silicon, silicon carbide, gallium nitride or aluminium nitride.

4. The SAW RFID sensor chip of claim 1, wherein said piezoelectric layer is made of zinc oxide, sapphire, aluminium nitride, lithium tantalate, lithium niobate, potassium niobate, lanthanum gallium silicate, silicon, silicon carbide or quartz.

5. The SAW RFID sensor chip of claim 1, wherein said multilayer heterojunction structure contains one GaN buffer layer at the bottom and one AlGaN barrier layer at the top, said AlGaN barrier layer having (i) thickness of 5-9 nanometres (nm), corresponding to the pseudo-conducting current range between the normally-on and normally-off operation mode of the formed 2DEG channel, and (ii) surface roughness of 0.2 nm or less.

6. The SAW RFID sensor chip of claim 5, wherein the thickness of the AlGaN barrier layer is 6-7 nm, preferably 6.2-6.4 nm, and the surface roughness of said AlGaN barrier layer is about 0.1 nm or less, preferably about 0.05 nm or less.

7. The SAW RFID sensor chip of claim 1, wherein said multilayer heterojunction structure is sandwich-like containing one GaN buffer layer at the top, one GaN buffer layer at the bottom and one AlGaN barrier layer in between, said 2DEG conducting channel being formed in the top GaN buffer layer above the AlGaN barrier layer, close to the interface between said top GaN buffer layer and said AlGaN barrier layer, thereby resulting in a N-face polarity of said structure, said top GaN buffer layer having (i) thickness of 5-9 nanometres (nm), corresponding to the pseudo-conducting current range between the normally-on and normally-off operation mode of the formed 2DEG channel, and (ii) surface roughness of 0.2 nm or less.

8. The SAW RFID sensor chip of claim 7, wherein the thickness of the top GaN buffer layer is 6-7 nm, preferably 6.2-6.4 nm, and the surface roughness of said AlGaN barrier layer is about 0.1 nm or less, preferably about 0.05 nm or less.

9. The SAW RFID sensor chip of claim 1, wherein said multilayer heterojunction structure is sandwich-like containing one GaN buffer layer at the top, one GaN buffer layer at the bottom and one AlGaN barrier layer in between, said 2DHG conducting channel being formed in the top GaN buffer layer above the AlGaN barrier layer, close to the interface between said top GaN buffer layer and said AlGaN barrier layer, thereby resulting in a Ga-face polarity of said structure, said top GaN buffer layer having (i) thickness of 5-9 nanometres (nm), which corresponds to the pseudo-conducting current range between the normally-on and normally-off operation mode of the formed 2DHG channel, and (ii) surface roughness of 0.2 nm or less.

10. The SAW RFID sensor chip of claim 9, wherein the thickness of the top GaN buffer layer is 6-7 nm, preferably 6.2-6.4 nm, and the surface roughness of said AlGaN barrier layer is about 0.1 nm or less, preferably about 0.05 nm or less.

11. The SAW RFID sensor chip of claim 1, further comprising an excitation light source for irradiating said piezoelectric substrate, thereby inducing an electric current in said 2DEG or 2DHG channel.

12. The SAW RFID sensor chip of claim 11, wherein said excitation light source is a surface-mounted-device light-emitting diode (SMD LED) or UV-VIS-IR laser diode.

13. The SAW RFID sensor chip of claim 1, wherein said metal IDTs are capable of receiving the RF signal of about 0.5-2.5 GHz and exhibiting the piezoelectric effect by creating acoustic waves over the surface of said piezoelectric substrate.

14. A sensing device with a remote readout, for material and structure sensing, comprising:
    the SAW RFID sensor chip of claim 1, inserted in a sensing device frame and connected to an electric circuit;
    at least one out-input SAW-RFID fractal antenna connected to said electric circuit, for receiving or transmitting a signal;

an output-input separation by delay line SAW transducer; and a remote integrated circuit for storing and processing said signal, and for modulating and demodulating a radio-frequency (RF) signals, said remote integrated circuit comprising:
  a) a voltage source supplying electric current to said SAW RFID sensor chip and to said out-input SAW-RFID fractal antenna/s;
  b) an integrated or CMOS current amplifier for amplification of an electric current obtained from said SAW RFID sensor chip;
  c) an analogue-to-digital converter with wireless input/output modules connected to said current amplifier for wireless outputting the converted signal to a user interface or external memory;
  d) a microcontroller unit (MCU) for processing and converting the received signal into data readable in said user interface or external memory; and
  e) a wireless connection module for wireless connection of said sensing device to said user interface or external memory.

15. The sensing device with a remote readout, for material and structure sensing, comprising:

the SAW RFID sensor chip of claim 11, inserted in a sensing device frame and connected to an electric circuit;

a modulated light source for irradiating the surface of the pseudo-conducting 2DEG or 2DHG structures of said SAW RFID sensor chip;

optocoupler switches for coupling said modulated light source with said pseudo-conducting 2DEG or 2DHG structures of the SAW RFID sensor chip;

a voltage source connected to said electrical circuit for supplying electric current to said SAW RFID sensor chip;

a lock-in amplifier connected to said voltage source for amplification of a signal with a known carrier wave obtained from said SAW RFID sensor chip, and for increasing the signal-to-noise ratio; and an analogue-to-digital converter (ADC) with in-built digital input/output card connected to said lock-in amplifier for outputting the converted signal to a user interface or external memory.

16. The sensing device of claim 14, wherein (i) said external memory is a mobile device, desktop computer, server, remote storage, internet storage or material diagnostics cloud; or (ii) said voltage source is a battery of the Li-ion type or energy harvester with AC-DC or DC-DC converters; or (iii) said current amplifier is connected in-line; or (iv) said wireless connection module is a short-range Bluetooth® or NFC module providing wireless communication between said sensing device and the user interface or external memory, or a Wi-Fi module providing wireless communication between said sensing device and the user interface or external memory, or a GSM module providing a worldwide wireless communication between said sensing device and the external memory.

17. The sensing device of claim 15, wherein (i) said external memory is a mobile device, desktop computer, server, remote storage, internet storage or material diagnostics cloud; or (ii) said voltage source is a battery of the Li-ion type or energy harvester with AC-DC or DC-DC converters; or (iii) said modulated light source is a surface-mounted-device light-emitting diode (SMD LED) or UV-VIS-IR laser diode.

18. A method for material and structure sensing comprising:
  1) Applying the sensing device of claim 14 to a material or structure to be sensed;
  2) Recording signals received from the material or structure in a form of a S21-transfer parameter dynamics of the device over time with said device;
  3) Transmitting the recorded signals from said device to the external memory for further processing; and
  4) Converting the transmitted signals to digital signals, processing the digital signals in the external memory, correlating said S21-transfer dynamics with pre-calibrated material or structure waveforms stored in the external memory, and extracting the material or structure information from said waveforms in a form of readable data.

19. A method for material and structure sensing comprising:
  1) Applying the sensing device of claim 15 to a material or structure to be sensed;
  2) Recording signals received from the material or structure in a form of a S21-transfer parameter dynamics of the device over time with said device;
  3) Transmitting the recorded signals from said device to the external memory for further processing; and
  4) Converting the transmitted signals to digital signals, processing the digital signals in the external memory, correlating said S21-transfer dynamics with pre-calibrated material or structure waveforms stored in the external memory, and extracting the material or structure information from said waveforms in a form of readable data.

20. The sensing device of claim 1, wherein said device is an ultrasensitive microphone.

* * * * *